US008417366B2

(12) United States Patent  
Getto et al.

(10) Patent No.: US 8,417,366 B2  
(45) Date of Patent: *Apr. 9, 2013

(54) COMPENSATION ORTHODONTIC ARCHWIRE DESIGN

(75) Inventors: Phillip Getto, Plano, TX (US); Rohit Sachdeva, Plano, TX (US); Peer Sporbert, Berlin (DE)

(73) Assignee: Orametrix, Inc., Richardson, TX (US)

( * ) Notice: Subject to any disclaimer, the term of this patent is extended or adjusted under 35 U.S.C. 154(b) by 414 days.

This patent is subject to a terminal disclaimer.

(21) Appl. No.: 12/772,178

(22) Filed: May 1, 2010

(65) Prior Publication Data

US 2011/0270583 A1 Nov. 3, 2011

(51) Int. Cl.  
*G06F 19/00* (2011.01)

(52) U.S. Cl. .............................. 700/98; 433/20

(58) Field of Classification Search ............. 700/98; 703/1

See application file for complete search history.

(56) References Cited

U.S. PATENT DOCUMENTS

2006/0079981 A1* 4/2006 Rubbert et al. ............... 700/98

* cited by examiner

*Primary Examiner* — Ryan Jarrett  
(74) *Attorney, Agent, or Firm* — Jasvantrai C. Shah

(57) ABSTRACT

Method and workstation automatically designing an archwire including compensations for auxiliary appliances or biological constraints exerting unknown forces to achieve a preplanned treatment goal are disclosed. The adjusted customized arch-wire is designed after an initial customized arch-wire has been used to treat a patient and is at or near equilibrium. The initial custom arch-wire is first designed by producing a 3D computer-based, geometrical model of a patient's dentition, locating brackets on the digital tooth model, moving the digital tooth models to planned final positions and orientations, and then calculating a wire which fits in the slots of the brackets while the teeth are in their planned final positions and exerts no forces on the brackets. After a period of time the teeth will move under the force of the wire and will eventually move into positions such that the forces from all appliances and biological systems are in equilibrium. If the teeth are not in the final planned positions at that point in time, the adjusted custom arch-wire is designed and applied.

15 Claims, 17 Drawing Sheets

COMPENSATION ORTHODONTIC ARCHWIRE DESIGN

CROSS-REFERENCE TO RELATED APPLICATIONS

This application is related to application Ser. No. 12/772,133, filed Apr. 30, 2010, Title: BRACKET-SLOT-TO-WIRE PLAY COMPENSATION ARCHWIRE DESIGN, and application Ser. No. 10/428,461, filed May 2, 2003, pending, which is a continuation-in-part of application Ser. No. 09/834,412, filed Apr. 13, 2001, now issued as U.S. Pat. No. 6,632,089, the entire contents of which are incorporated by reference herein. This application is also related to patent application Ser. No. 10/429,123, filed May 2, 2003, now issued as U.S. Pat. No. 7,234,937, the entire contents of which are incorporated by reference herein. This application is also related to application Ser. No. 09/835,039, filed Apr. 13, 2001, now issued as U.S. Pat. No. 6,648,640, the entire contents of which are incorporated by reference herein.

BACKGROUND OF THE INVENTION

A. Field of the Invention

This invention relates generally to the field of orthodontics. More particularly, the invention relates to designing an adjusted customized arch-wire after an initial customized arch-wire has been used to treat a patient and is at or near equilibrium but the patient's teeth have not reached the target position. The adjusted customized archwire is designed by compensating the initial design based upon the tooth displacement for one or more teeth required in the progress model.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. Corrections to the bracket position and/or wire shape are made manually by the orthodontist.

The key to efficiency in treatment and maximum quality in results is a realistic simulation of the treatment process. Today's orthodontists have the possibility of taking plaster models of the upper and lower jaw, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per jaw that covers all brackets and relevant portions of every tooth. Using such a transfer tray guarantees a very quick and yet precise bonding using indirect bonding.

However, it is obvious that such an approach requires an extreme amount of time and labor and thus is too costly, and this is the reason why it is not practiced widely. The normal orthodontist does not fabricate set-ups; he places the brackets directly on the patient's teeth to the best of his knowledge, uses an off-the-shelf wire and hopes for the best. There is no way to confirm whether the brackets are placed correctly; and misplacement of the bracket will change the direction and/or magnitude of the forces imparted on the teeth. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. And the patient has no choice and does not know that treatment time could be significantly reduced if proper planning was done.

U.S. Pat. No. 5,431,562 to Andreiko et al. describes a computerized, appliance-driven approach to orthodontics. In this method, first certain shape information of teeth is acquired. A uniplanar target archform is calculated from the shape information. The shape of customized bracket slots, the bracket base, and the shape of an orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, in the late 1990's Align Technologies began offering transparent, removable aligning devices as a new treatment modality in orthodontics. In this system, a plaster model of the dentition of the patent is obtained by the orthodontist and shipped to a remote appliance manufacturing center, where it is scanned with a laser. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

U.S. Pat. No. 6,632,089 to Rubbert discloses an interactive, software-based treatment planning method to correct a malocclusion. The method can be performed on an orthodontic workstation in a clinic or at a remote location such as a lab or precision appliance manufacturing center. The workstation stores a virtual three-dimensional model of the dentition of a patient and patient records. The virtual model is manipulated by the user to define a target situation for the patient, including a target archform and individual tooth positions in the archform. Parameters for an orthodontic appliance, such as the location of orthodontic brackets and resulting shape of a customized orthodontic archwire, are obtained from the simulation of tooth movement to the target situation and the placement position of virtual brackets. However, often, the effectiveness of a customized archwire reaches an equilibrium at some point in time where the archwire ceases to exert force on the teeth even though the teeth have not yet attained the desired target position. Therefore a need exists to for adjusting the design of a customized archwire by compensating the initial design based upon tooth displacements called for in the progress model of the patient with respect to the target model where the teeth should ultimately reach indicating the end of the treatment. The present invention meets this need.

SUMMARY OF THE INVENTION

Often, the initially designed customized archwire for moving a patient's teeth from malocclusion to the desired target set-up reaches an equilibrium without achieving the planned treatment goal. In such a case the current or progress model of the patient's teeth shows tooth displacements required to achieve the target positions. The preferred embodiment of the invention disclosed herein enables the practitioner evaluate the progress model in order to determine the tooth displacements still required to move the teeth in the desired positions; and design the compensation archwire by making adjustments necessary to the initial design of the arch wire. The compensations can be made to achieve displacements in all 6 degrees of freedom, i.e. misial or distal translational displacement, buccal or lingual translational displacement; occlusal or gingival translational displacement, facial or lingual torque, mesial or distal angulation and mesial or distal rotation. The treatment planning software performs calculations automatically to determine the extent and the nature of displacements required from the three dimensional digital models of progress and the target. The practitioner can look at the displacements and if they are satisfactory, then instructs the workstation to perform the compensation design of the archwire automatically. The workstation provides the tools whereby the practitioner can override one or more displacements that were automatically calculated by the treatment planning workstation; and specify new values for the selected displacements. Then the compensation archwire design is performed using the displacement parameters specified by the practitioner or the treatment planner.

BRIEF DESCRIPTION OF THE DRAWINGS

Presently preferred embodiments of the invention are described below in reference to the appended drawings, wherein like reference numerals refer to like elements in the various views, and in which:

FIG. 5 also shows the slot for the bracket associated with the tooth and the archwire cross-section rotated to deliver the desired facial torque.

FIG. 6 shows the same example tooth as in FIG. 5. However, the practitioner overrides the automatic determination by the treatment planning software and changes the torque to a lingual torque. FIG. 6 shows the same slot for the bracket as in FIG. 5 associated with the tooth. However, the archwire cross-section is now rotated in the lingual direction to deliver the desired lingual torque.

FIG. 8B is similar to FIG. 8A with the exception that FIG. 8B shows that a tooth requires a distal angulation. In this case, the straight archwire segment is rotated around the y-axis in the distal direction such that the straight archwire segment makes surface contact with the walls of the bracket slot at two locations. This type and amount of offset would provide the desired degree of distal angulation.

FIG. 15 shows the virtual superimposed model the same as in FIG. 13 along with the newly designed compensation archwire.

DETAILED DESCRIPTION OF PREFERRED EMBODIMENT

Before describing the features of this invention in detail, an overview of a unified workstation will be set forth initially.

The workstation provides software features that create two dimensional and/or three-dimensional virtual patient model on a computer, which can be used for purposes of treatment planning in accordance with a presently preferred embodiment.

Many of the details and computer user interface tools which a practitioner may use in adjusting tooth position, designing appliance shape and location, managing space between teeth, and arriving at a finish tooth position using interaction with a computer storing and displaying a virtual model of teeth are set forth in the prior application Ser. No. 09/834,412 filed Apr. 13, 2001, and in published OraMetrix patent application WO 01/80761, the contents of which are incorporated by reference herein. Other suites of tools and functions are possible and within the scope of the invention. Such details will therefore be omitted from the present discussion.

General Description

A unified workstation environment and computer system for diagnosis, treatment planning and delivery of therapeutics, especially adapted for treatment of craniofacial structures, is described below. In one possible example, the system is particularly useful in diagnosis and planning treatment of an orthodontic patient. Persons skilled in the art will understand that the invention, in its broader aspects, is applicable to other craniofacial disorders or conditions requiring surgery, prosthodontic treatment, restorative treatment, etc.

Figure 1:
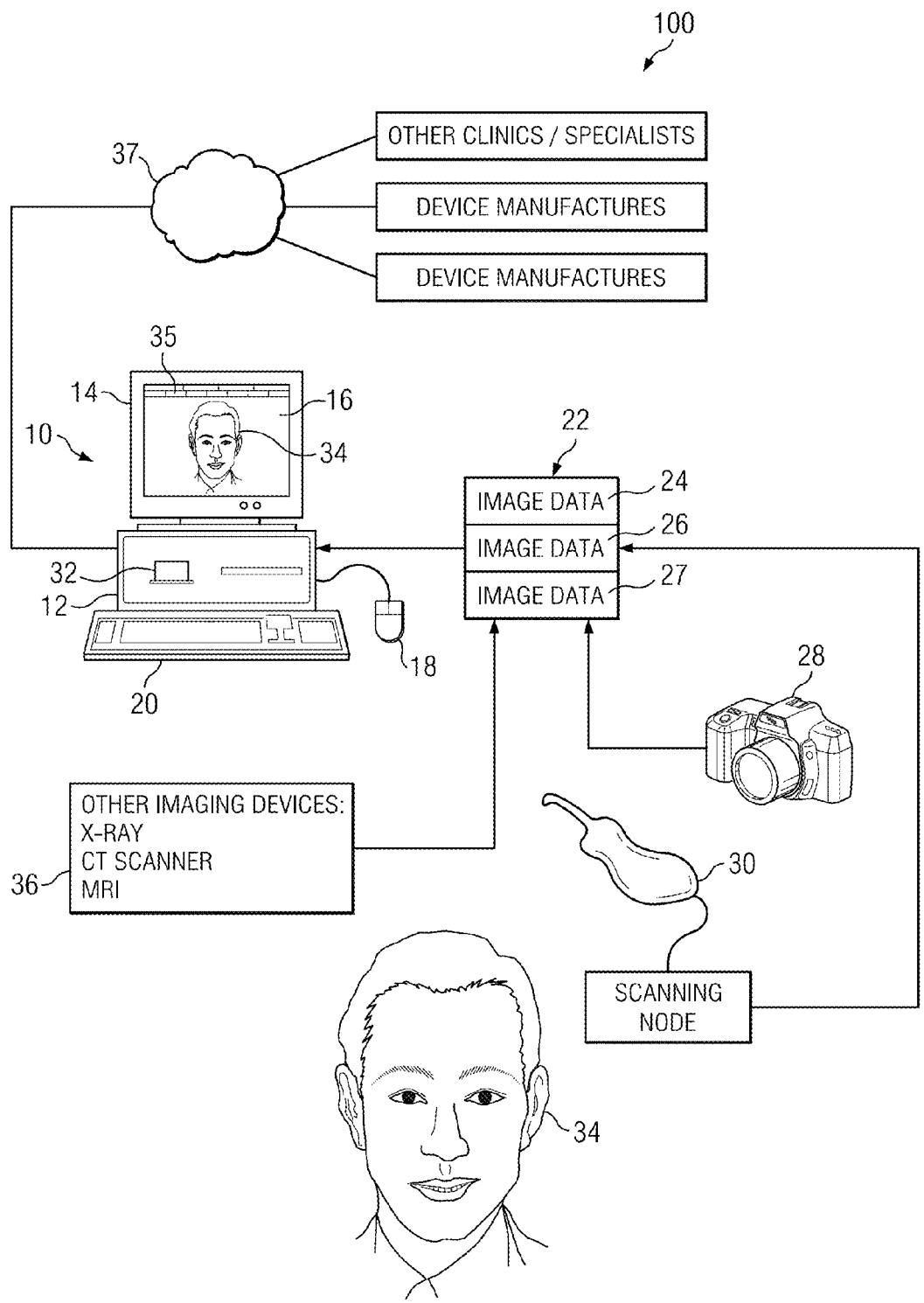
FIG. 1 is block diagram of a system for creating a three-dimensional virtual patient model and for diagnosis and planning treatment of the patient.

A presently preferred embodiment is depicted in FIG. 1. The overall system 100 includes a general-purpose computer system 10 having a processor (CPU 12) and a user interface 14, including screen display 16, mouse 18 and keyboard 20. The system is useful for planning treatment for a patient 34.

The system 100 includes a computer storage medium or memory 22 accessible to the general-purpose computer system 10. The memory 22, such as a hard disk memory or attached peripheral devices, stores two or more sets of digital data representing patient craniofacial image information. These sets include at least a first set of digital data 24 representing patient craniofacial image information obtained from a first imaging device and a second set of digital data 26 representing patient craniofacial image information obtained from a second image device different from the first image device. The first and second sets of data represent, at least in part, common craniofacial anatomical structures of the patient. At least one of the first and second sets of digital data normally would include data representing the external visual appearance or surface configuration of the face of the patient.

In a representative and non-limiting example of the data sets, the first data set 24 could be a set of two dimensional color photographs of the face and head of the patient obtained via a color digital camera 28, and the second data set is three-dimensional image information of the patient's teeth, acquired via a suitable scanner 30, such as a hand-held optical 3D scanner, or other type of scanner. The memory 22 may also store other sets 27 of digital image data, including digitized X-rays, MRI or ultrasound images, CT scanner etc., from other imaging devices 36. The other imaging devices need not be located at the location or site of the workstation system 100. Rather, the imaging of the patient 34 with one or other imaging devices 36 could be performed in a remotely located clinic or hospital, in which case the image data is obtained by the workstation 100 over the Internet 37 or some other communications medium, and stored in the memory 22.

The system 100 further includes a set of computer instructions stored on a machine-readable storage medium. The instructions may be stored in the memory 22 accessible to the general-purpose computer system 10. The machine-readable medium storing the instructions may alternatively be a hard disk memory 32 for the computer system 10, external memory devices, or may be resident on a file server on a network connected to the computer system, the details of which are not important. The set of instructions, described in more detail below, comprise instructions for causing the general computer system 10 to perform several functions related to the generation and use of the virtual patient model in diagnostics, therapeutics and treatment planning.

These functions include a function of automatically, and/or with the aid of operator interaction via the user interface 14, superimposing the first set 24 of digital data and the second set 26 of digital data so as to provide a composite, combined digital representation of the craniofacial anatomical structures in a common coordinate system. This composite, combined digital representation is referred to herein occasionally as the "virtual patient model," shown on the display 16 of FIG. 1 as a digital model of the patient 34. Preferably, one of the sets 24, 26 of data includes photographic image data of the patient's face, teeth and head, obtained with the color digital camera 28. The other set of data could be intra-oral 3D scan data obtained from the hand-held scanner 30, CT scan data, X-Ray data, MRI, etc. In the example of FIG. 1, the hand-held scanner 30 acquires a series of images containing 3D information and this information is used to generate a 3D model in the scanning node 31, in accordance with the teachings of the published PCT application of OraMetrix, PCT publication no. WO 01/80761, the content of which is incorporated by reference herein. Additional data sets are possible, and may be preferred in most embodiments. For example the virtual patient model could be created by a superposition of the following data sets: intra-oral scan of the patient's teeth, gums, and associated tissues, X-Ray, CT scan, intra-oral color photographs of the teeth to add true color (texture) to the 3D teeth models, and color photographs of the face, that are combined in the computer to form a 3D morphable face model. These data sets are superimposed with each other, with appropriate scaling as necessary to place them in registry with each other and at the same scale. The resulting representation can be stored as a 3D point cloud representing not only the surface on the patient but also interior structures, such as tooth roots, bone, and other structures. In one possible embodiment, the hand-held in-vivo scanning device is used which also incorporates a color CCD camera to capture either individual images or video.

The software instructions further includes a set of functions or routines that cause the user interface 16 to display the composite, combined digital three-dimensional representation of craniofacial anatomical structures to a user of the system. In a representative embodiment, computer-aided design (CAD)-type software tools are used to display the model to the user and provide the user with tools for viewing and studying the model. Preferably, the model is cable of being viewed in any orientation. Tools are provided for showing slices or sections through the model at arbitrary, user defined planes. Alternatively, the composite digital representation may be printed out on a printer or otherwise provided to the user in a visual form.

The software instructions further include instructions that, when executed, provide the user with tools on the user interface 14 for visually studying, on the user interface, the interaction of the craniofacial anatomical structures and their relationship to the external, visual appearance of the patient. For example, the tools include tools for simulating changes in the anatomical position or shape of the craniofacial anatomical structures, e.g., teeth, jaw, bone or soft tissue structure, and their effect on the external, visual appearance of the patient.

The preferred aspects of the software tools include tools for manipulating various parameters such as the age of the patient; the position, orientation, color and texture of the teeth; reflectivity and ambient conditions of light and its effect on visual appearance. The elements of the craniofacial and dental complex can be analyzed quickly in either static format (i.e., no movement of the anatomical structures relative to each other) or in an dynamic format (i.e., during movement of anatomical structures relative to each other, such as chewing, occlusion, growth, etc.). To facilitate such modeling and simulations, teeth may be modeled as independent, individually moveable 3 dimensional virtual objects, using the techniques described in the above-referenced OraMetrix published PCT application, WO 01/80761.

The workstation environment provided by this invention provides a powerful system and for purposes of diagnosis, treatment planning and delivery of therapeutics. For example, the effect of jaw and skull movement on the patient's face and smile can be studied. Similarly, the model can be manipulated to arrive at the patient's desired feature and smile. From this model, and more particularly, from the location and position of individual anatomical structures (e.g., individual tooth positions and orientation, shape of arch and position of upper and lower arches relative to each other), it is possible to automatically back solve for or derive the jaw, tooth, bone and/or soft tissue corrections that must be applied to the patient's initial, pre-treatment position to provide the desired result. This leads directly to a patient treatment plan.

These simulation tools, in a preferred embodiment, comprise user-friendly and intuitive icons 35 that are activated by a mouse or keyboard on the user interface of the computer system 10. When these icons are activated, the software instruction provide pop-up, menu, or other types screens that enable a user to navigate through particular tasks to highlight and select individual anatomical features, change their positions relative to other structures, and simulate movement of the jaws (chewing or occlusion). Examples of the types of navigational tools, icons and treatment planning tools for a computer user interface that may be useful in this process and provide a point of departure for further types of displays useful in this invention are described in the patent application of Rudger Rubbert et al., Ser. No. 09/835,039 filed Apr. 13, 2001, the contents of which are incorporated by reference herein.

The virtual patient model, or some portion thereof, such as data describing a three-dimensional model of the teeth in initial and target or treatment positions, is useful information for generating customized orthodontic appliances for treatment of the patient. The position of the teeth in the initial and desired positions can be used to generate a set of customized brackets, and customized flat planar archwire, and customized bracket placement jigs, as described in the above-referenced Andreiko et al. patents. Alternatively, the initial and final tooth positions can be used to derive data sets representing intermediate tooth positions, which are used to fabricate transparent aligning shells for moving teeth to the final position, as described in the above-referenced Chisti et al. patents. The data can also be used to place brackets and design a customized archwire as described in the previously cited application Ser. No. 09/835,039.

To facilitate sharing of the virtual patient model among specialists and device manufacturers, the system 100 includes software routines and appropriate hardware devices for transmitting the virtual patient model or some subset thereof over a computer network. The system's software instructions are preferably integrated with a patient management program having a scheduling feature for scheduling appointments for the patient. The patient management program provides a flexible scheduling of patient appointments based on progress of treatment of the craniofacial anatomical structures. The progress of treatment can be quantified. The progress of treatment can be monitored by periodically obtaining updated three-dimensional information regarding the progress of treatment of the craniofacial features of the patient, such as by obtaining updated scans of the patient and comparison of the resulting 3D model with the original 3D model of the patient prior to initiation of treatment.

Thus, it is contemplated that system described herein provides a set of tools and data acquisition and processing subsystems that together provides a flexible, open platform or portal to a variety of possible therapies and treatment modalities, depending on the preference of the patient and the practitioner. For example, a practitioner viewing the model and using the treatment planning tools may determine that a patient may benefit from a combination of customized orthodontic brackets and wires and removable aligning devices. Data from the virtual patient models is provided to diverse manufacturers for coordinated preparation of customized appliances. Moreover, the virtual patient model and powerful tools described herein provide a means by which the complete picture of the patient can be shared with other specialists (e.g., dentists, maxilla-facial or oral surgeons, cosmetic surgeons, other orthodontists) greatly enhancing the ability of diverse specialists to coordinate and apply a diverse range of treatments to achieve a desired outcome for the patient. In particular, the overlay or superposition of a variety of image information, including 2D X-Ray, 3D teeth image data, photographic data, CT scan data, and other data, and the ability to toggle back and forth between these views and simulate changes in position or shape of craniofacial structures, and the ability to share this virtual patient model across existing computer networks to other specialists and device manufacturers, allows the entire treatment of the patient to be simulated and modeled in a computer. Furthermore, the expected results can be displayed before hand to the patient and changes made depending on the patient input.

With the above general description in mind, additional details of presently preferred components and aspects of the inventive system and the software modules providing the functions referenced above will be described next.

Bracket-Slot-to-Wire Play Compensation

For orthodontic treatment of a patient, orthodontic archwires are used to apply forces to brackets bonded onto the patient's teeth to move the teeth into the desired positions for achieving the target of the treatment. The archwire is inserted into the bracket slots; therefore it is of a smaller cross-section than the bracket slots.

During the treatment planning process, customized archwires are designed based upon the individual treatment goals (target positions of teeth) and individual bracket positions on the teeth to increase the effectiveness of the archwires in achieving the treatment goals. Customized archwires comprise alternating sliding segments interconnected by segments with bends and/or twists in three-dimensional space. Sliding segments may comprise either straight or smoothly curved segments or a combination thereof. The sliding segments are placed in the bracket slots and exert forces on the brackets for moving the teeth towards the target positions. However, the effectiveness of a customized archwire can be reduced when one or more archwire segments fail to engage the bracket slots properly due to the extra space surrounding the archwire segments occupying the bracket slots, since the archwires cross-sections, as discussed above, are smaller in dimensions then the bracket slots they occupy. The space between a bracket slot and a sliding segment of the archwire occupying the bracket slot is hereinafter referred to as bracket-slot-to-wire play. The preferred embodiment of the invention disclosed herein teaches methods for offsetting the undesired effects of the bracket-slot-to-wire play by properly engaging the archwire in the bracket slots. The scope of the customized archwire design is expanded to include positioning the geometry of the archwire sliding segments in relation to the bracket slots in order to properly compensate for the bracket-slot-to-wire play.

Figure 2:
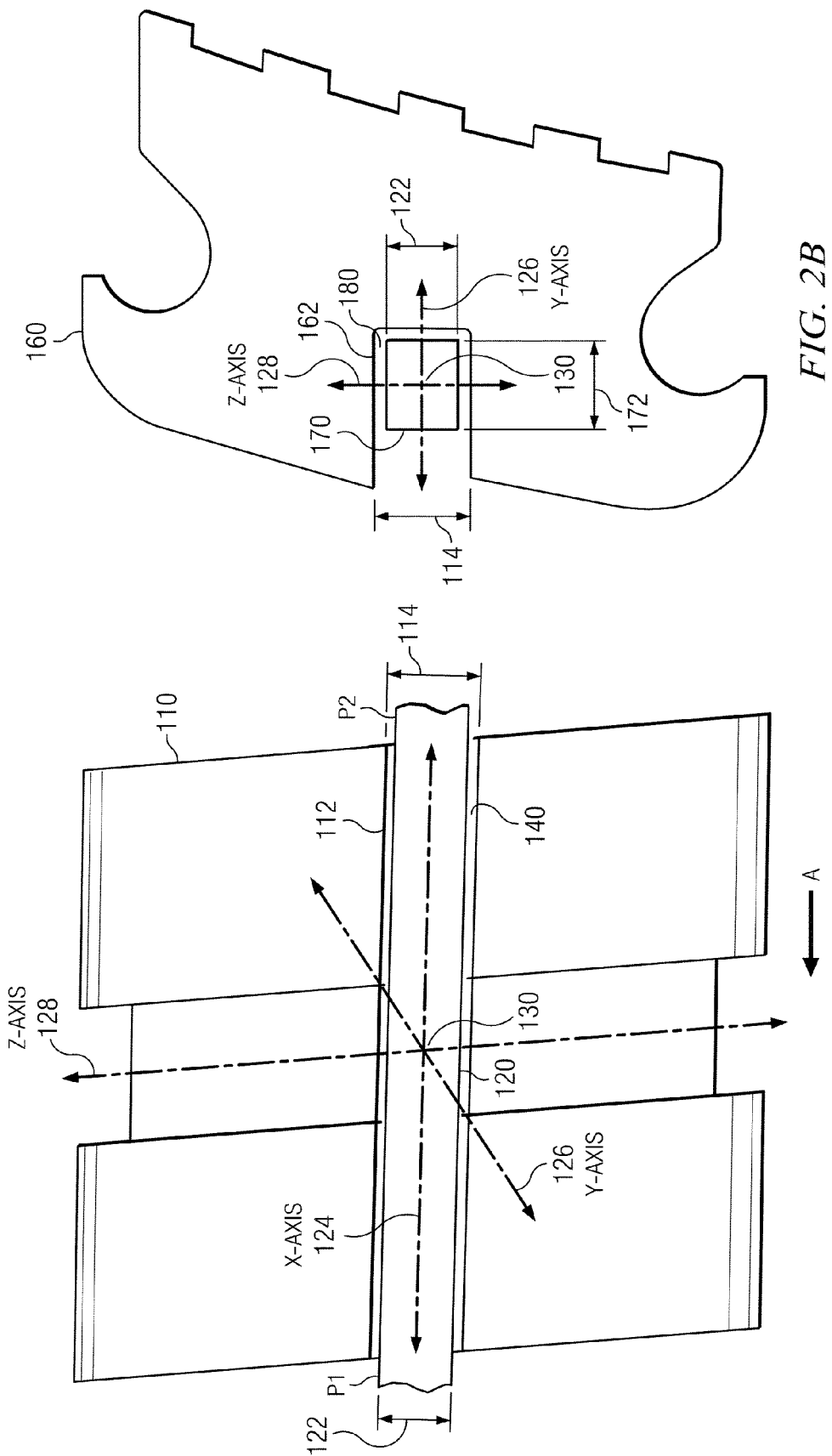
FIG. 2A shows the front-view of an example bracket and an example archwire sliding segment inserted in the slot of the bracket.
FIG. 2B shows a cross-sectional view of the bracket and the archwire sliding segment shown in FIG. 2A.

FIGS. 2A and 2B illustrate in detail the concept of the bracket-slot-to-wire play.

FIG. 2A shows the front-view of an example bracket 110 with slot 112 having the width 114. An example archwire sliding segment 120 having width 122 is inserted in the slot 112 of bracket 110. The archwire sliding segment 120 has x-axis 124, y-axis 126 and z-axis 128 with x-axis, y-axis and z-axis crossing at the center 130. Axes x, y and z are orthogonal to each other. The bracket-slot-to-wire play 140 in this case is the space between the bracket slot 112 and the archwire sliding segment 120.

FIG. 2B shows a cross-sectional view 160 of the bracket 110 and the cross-sectional view 170 of the archwire sliding segment 120, both shown in FIG. 2A, taken at the z-axis plane in FIG. 2A and viewed from the direction A. The sliding segment is generally straight, however, one skilled in the art would appreciate the sliding segment having a smoothly curved shape. The bracket slot cross-section 162 has the width 114 the same as in FIG. 2A. The archwire cross-section 170 has the width 122 the same as in FIG. 2A, and the height 172. For the archwire cross-section 170, the y-axis 126 and the z-axis 128 and the center 130 remain the same as in FIG. 2A. The bracket-slot-to-wire play 180 is the space surrounding the archwire cross-section 170 bounded by the bracket slot cross-section 162. Although the archwire cross-section 170 shown in FIG. 2B is rectangular in shape with sharp or unrounded edges, one skilled in the art would appreciate that the archwires with cross-sections having variety of geometrical shapes, such as for example, square with sharp edges, rectangular with rounded edges, square with rounded edges, elliptical, round, etc. are possible.

Figure 3:
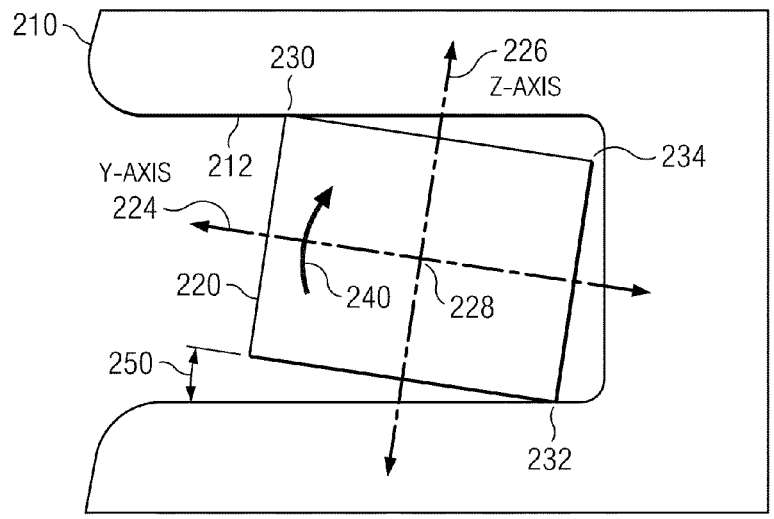
FIG. 3 is similar to FIG. 2B and shows the cross-section of the bracket and the archwire shown in FIG. 2A with the archwire rotated to apply torque.

As a typical deficiency, the bracket-slot-to-wire play prevents an archwire from exerting the desired torque to move a tooth in the facial or lingual direction. According to the preferred embodiment of the invention, this deficiency can be offset by properly rotating (or twisting) the sliding segment of the archwire along the long axis of the wire or x-axis. FIG. 3 shows an enlarged view of the cross-section of the bracket 210 which is similar to the bracket cross section 160 in FIG. 2B. In order to achieve the desired torque the sliding segment of the archwire going through the bracket slot 212 is rotated such that its cross-section 220 engages the walls of the bracket slot at points 230 and 232, and optionally at point 234 as well. In order to explain the nature of rotation a reference to FIGS. 2A and 2B will now be made. Imagine that in FIG. 2A, the archwire sliding segment 120 is rotated or twisted uniformly between the end points P1 and P2 of the archwire sliding segment 120 along the x-axis 124 until the diagonally opposite corner-points of the archwire cross-section 170 of FIG. 2B touch the walls of the bracket slot 162 in FIG. 2B. The same type of rotation as described above is made of the archwire having the cross-section 220 and around the center point 228 in FIG. 3. The direction of rotation 240 of the archwire causes the archwire cross-section 220 rotated by degrees identified by the angle 250. The y-axis 224 and the z-axis 226 moved as a result of the rotation in the positions shown in FIG. 3. One skilled in the art would appreciate that if the desired torque is facial torque than the rotation of the archwire would be in the facial direction; whereas if the desired torque is lingual, then the rotation of the archwire would be in the lingual direction, opposite to the direction for the facial torque.

Figure 4A:
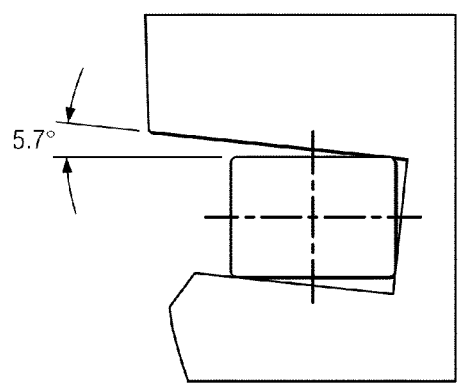
FIG. 4A shows an example bracket-slot with industry standard specification of width; and an example archwire with industry standard specification. The archwire has rectangular cross-section with sharp un-rounded edges.
Figure 4B:
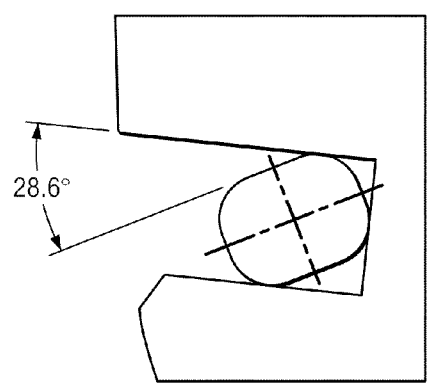
FIG. 4B shows an example bracket-slot and an example archwire with industry standard specifications the same as in FIG. 4A; however, the archwire in FIG. 4B has rectangular cross-section with rounded edges.

The amount of the bracket-slot-to-wire play is determined by the size of the bracket slot and the size of the archwire in terms of its cross section. The bracket slots are specified in terms of the width dimension with a tolerance; and the archwires are specified in terms of the cross-section and tolerances. One can use the data supplied by the manufacturers of the brackets and the archwires to compute the size of the bracket-slot-to-wire play. Alternately, one can scan the bracket and the archwire of interest to determine the actual size of the bracket slot and the archwire cross-section in order to determine the actual value of the bracket-slot-to-wire play. FIG. 4A shows an example bracket-slot with industry standard specification of width equal to 0.46 mm+0.04 mm tolerance; and an example archwire with cross-section of 0.41 mm−0.01 mm tolerance×0.56 mm−0.01 mm tolerance; and rounded edges with a small radius. The archwire has rectangular cross-section with sharp un-rounded edges (or edges rounded with a very small radius not shown in this figure). The degree of rotation of the sliding segment of the archwire that can be realized in this case is 5.7°. FIG. 4B shows the same bracket slot and the archwire combination as in FIG. 4A, with the exception that the archwire cross-section has rounded edges with a larger radius. The resulting degree of rotation of the sliding segment of the archwire that can be realized is 28.6°. One skilled in the art would appreciate the calculation of the bracket-slot-to-wire play required for a smoothly curved segment can be done at the first contact point of the wire and the bracket slot. In the symmetric case, this can be done at the midpoint of the sliding segment.

Figure 5:
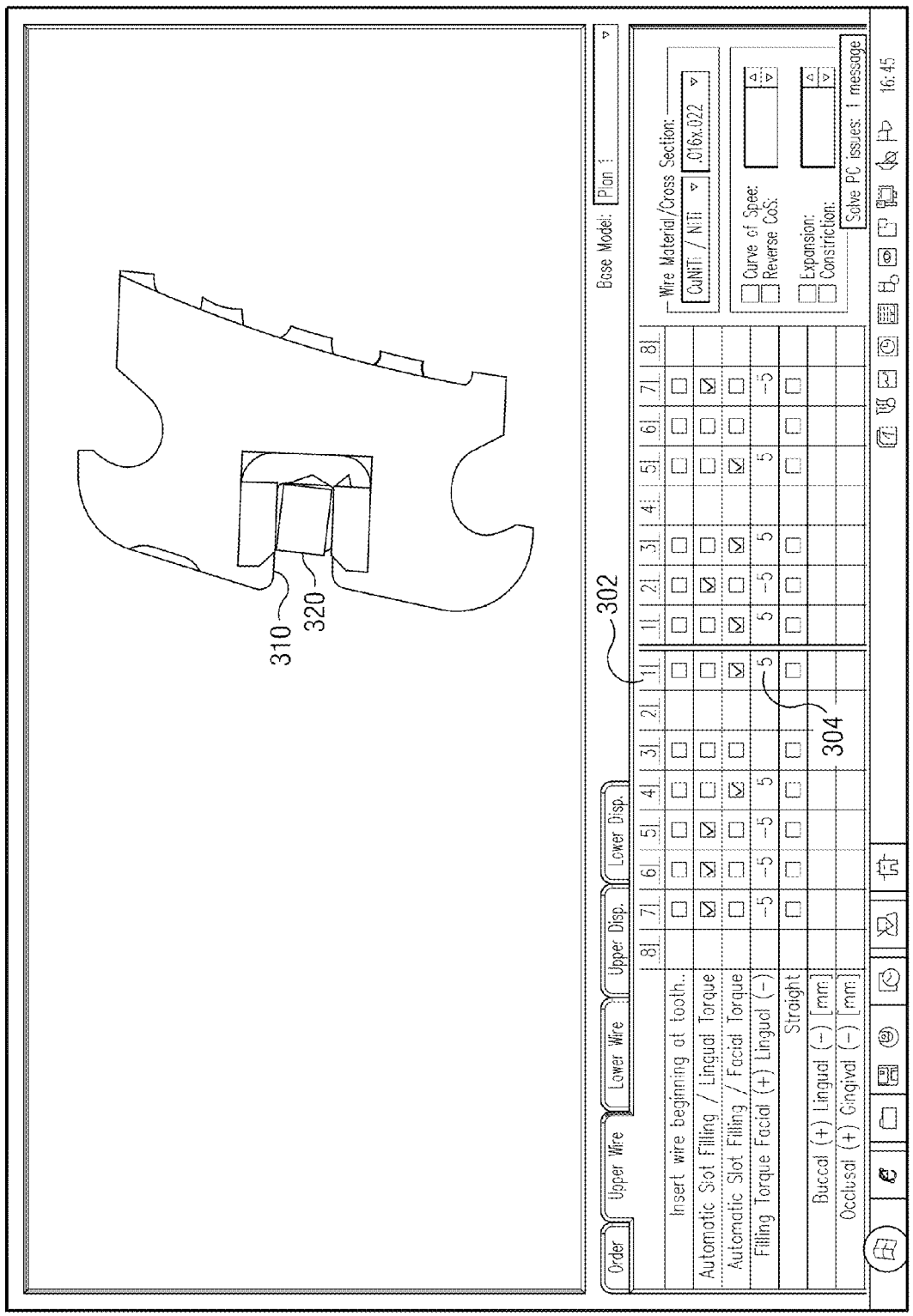
FIG. 5 shows an example where a tooth requires facial torque, which has been automatically calculated by the treatment planning software.

FIG. 5 shows an example where the tooth 302 requires facial torque and an additional slot-filling torque 304 in the amount of 5°, which has been automatically calculated by the treatment planning software to fully engage the bracket slot. FIG. 5 also shows the slot 310 for the bracket associated with tooth 302 and the archwire cross-section 320 rotated in the facial direction to fully engage the bracket.

Figure 6:
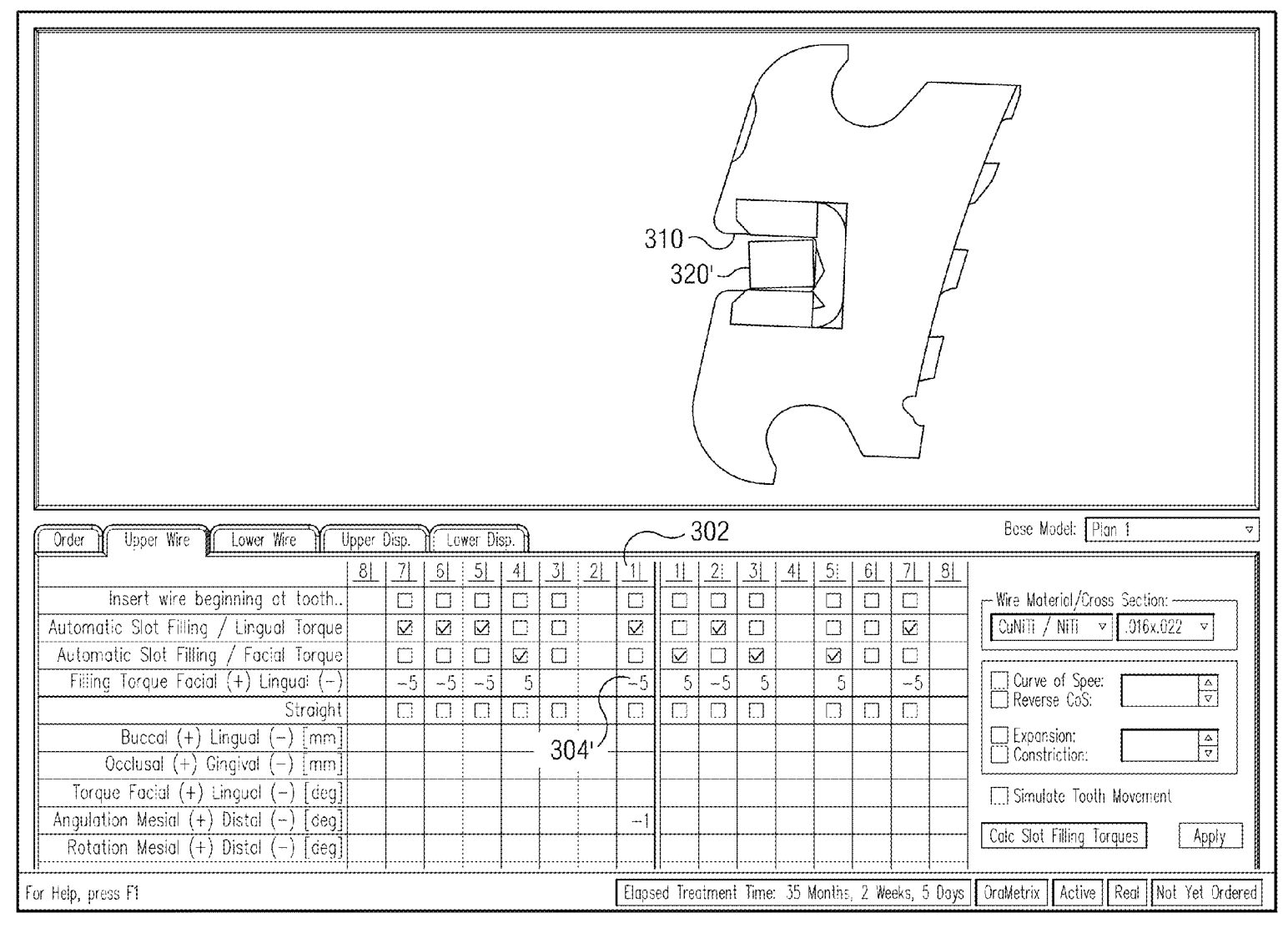

FIG. 6 shows the same example tooth 302 as in FIG. 5. However, if the practitioner desires lingual tooth movement, the automatic determination by the treatment planning software changes the additional slot-filling torque 304' to a lingual torque in the amount of −5°. FIG. 6 shows the same slot 310 for the bracket as in FIG. 5 associated with tooth 302. However, the archwire cross-section 320' is now rotated in the lingual direction to fully engage the bracket.

Figure 7:
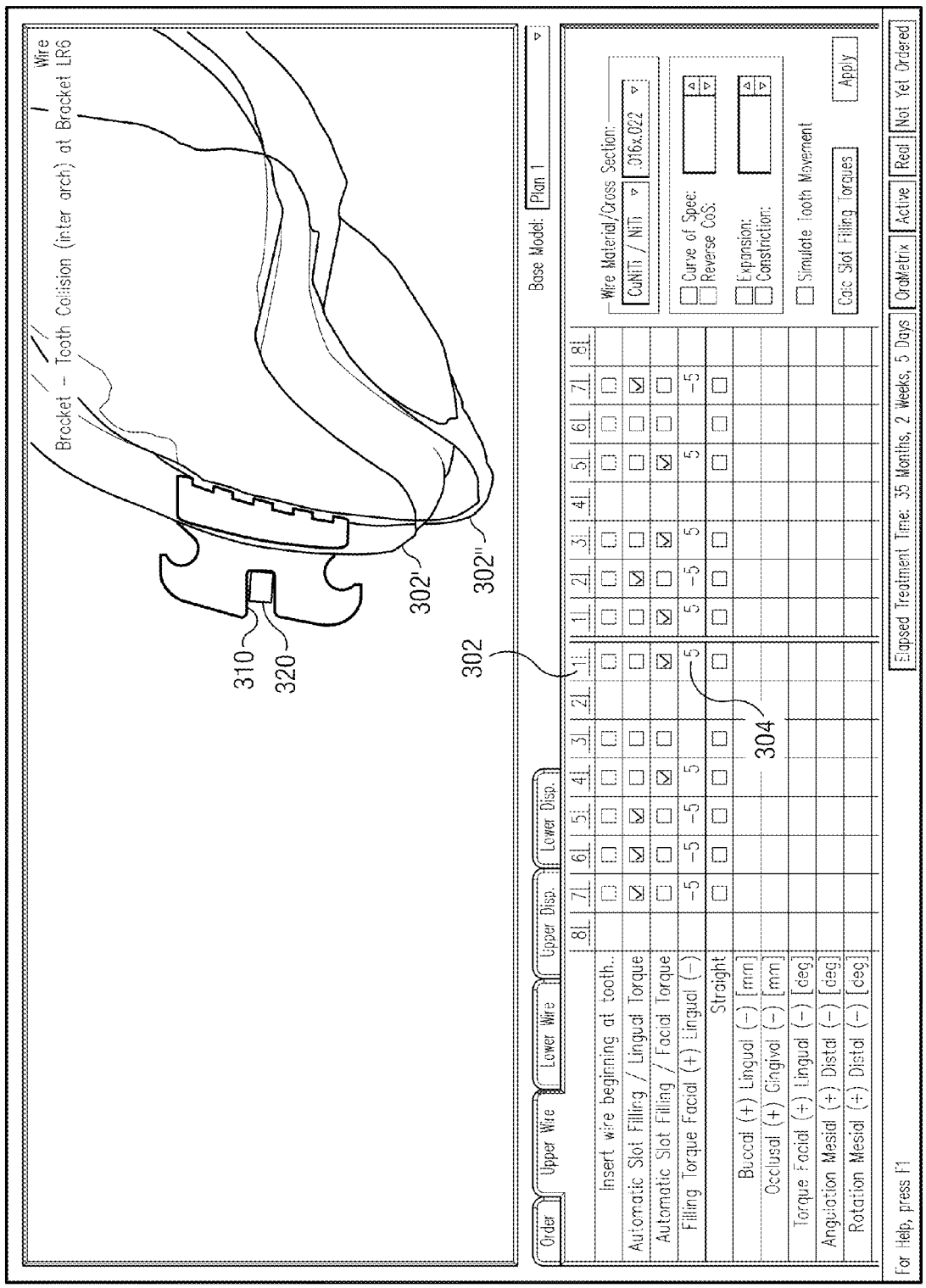
FIG. 7 shows the same example tooth as in FIG. 5. The tooth is shown in two different positions, namely the tooth in the target position superimposed over the tooth in the initial position, in FIG. 7. Also shown are the bracket and the archwire cross-section rotated to deliver facial torque.

FIG. 7 shows the same example tooth 302 as in FIG. 5. Tooth 302 is shown in two different positions, namely the tooth 302 in the target position 302" superimposed over the tooth 302 in the initial position 302'. The bracket with the slot 310 is shown bonded to the target position 302". The archwire cross-section 320 is shown in the rotated position just the same as in FIG. 5 for delivering the facial torque with the additional slot-filling torque 304 in the amount of 5°. The tooth 302 in the target position 302" superimposed over the tooth 302 in the initial position 302' is shown in the form of a cross-section made possible by the clipping plane tool in the treatment planning software.

Figure 8A:
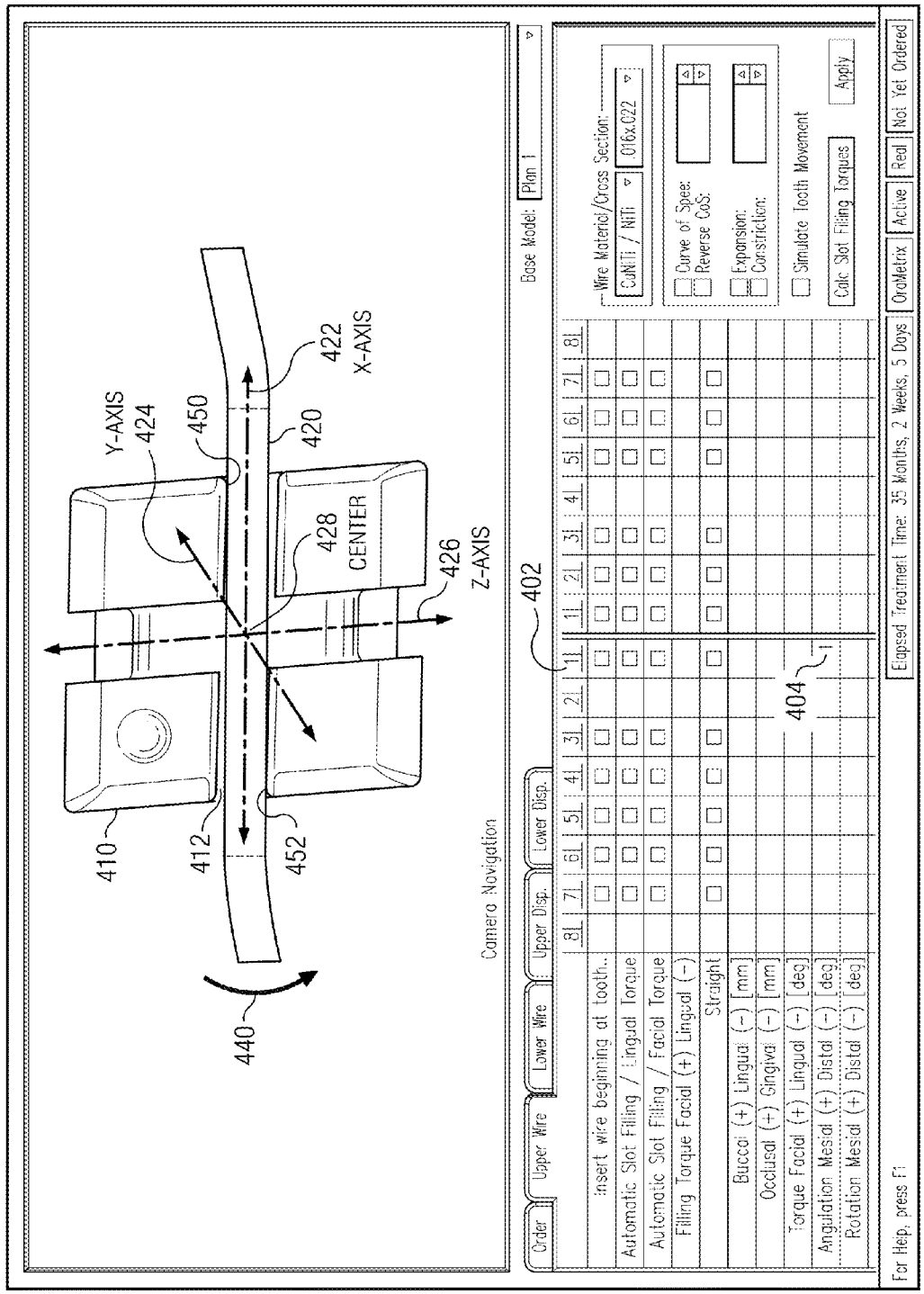
FIG. 8A shows that a tooth requires a mesial angulation. The straight archwire segment is rotated around the y-axis in the mesial direction such that the straight archwire segment makes surface contact with the walls of the bracket slot at two locations. This type and amount of offset would provide the desired degree of mesial angulation.

As another deficiency, the bracket-slot-to-wire play prevents an archwire from exerting the desired angulation force to move a tooth in the mesial or distal direction. According to another preferred embodiment of the invention, this deficiency can be offset by properly rotating the sliding segment of the archwire around the y-axis of the wire. FIG. 8A shows that a tooth 402 labeled as 1 requires an additional slot-filling mesial angulation 404 of 1°. Bracket 410 is associated with tooth 402. The bracket slot 412 is engaged by straight archwire segment 420. The straight archwire segment 420 has x-axis 422, y-axis 424, z-axis 426 and the center 428. In order to provide the desired mesial angulation, the straight archwire segment 420 is rotated around the center 428 in the rotation direction 440 such that the straight archwire segment 420 makes surface contact with the walls of the bracket slot 412 at locations 450 and 452.

Figure 8B:
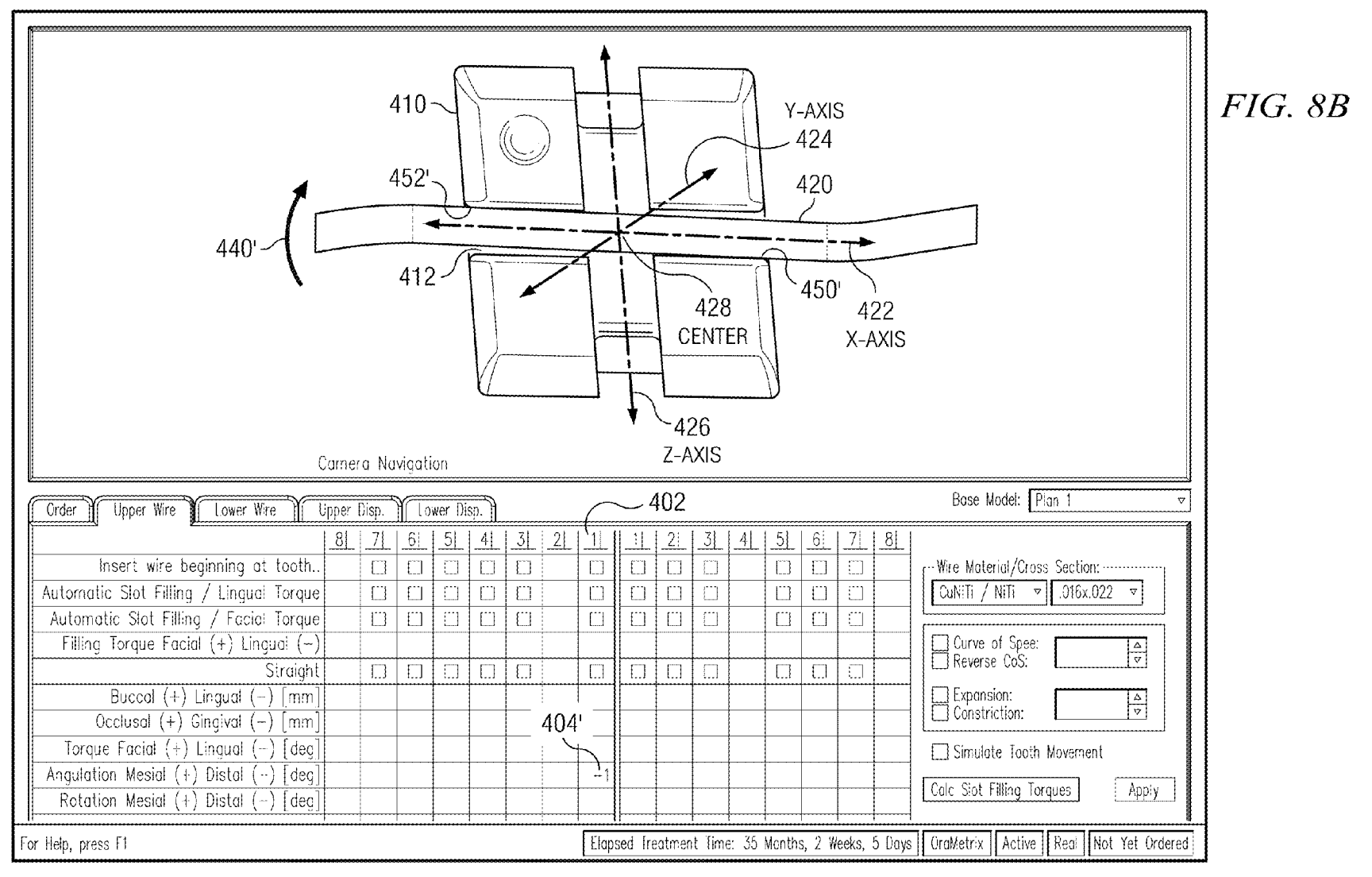

FIG. 8B is very similar to FIG. 8A, except that the tooth 402 labeled as 1 in this case requires an additional slot-filling distal angulation 404' of −1°. Bracket 410 remains associated with tooth 402. The bracket slot 412 is engaged by straight archwire segment 420. The straight archwire segment 420 has x-axis 422, y-axis 424, z-axis 426 and the center 428. In order to provide the desired mesial angulation, the straight archwire segment 420 is rotated around the center 428 in the rotation direction 440' such that the straight archwire segment 420 makes surface contact with the walls of the bracket slot 412 at locations 450' and 452'.

As yet another deficiency, the bracket-slot-to-wire play prevents an archwire from exerting the desired force to rotate a tooth in the mesial or distal direction. According to yet another preferred embodiment of the invention, this deficiency can be offset by properly rotating the sliding segment of the archwire around z-axis. In order to explain this embodiment of the invention, reference is made back to FIG. 2A. The archwire sliding segment 120 is rotated around the z-axis 128 either in the mesial direction if the mesial rotation is desired, or in the distal direction if the distal rotation is desired, until the archwire comes in firm contact with the bottom wall of the bracket-slot occupied by the archwire.

As yet another deficiency, the bracket-slot-to-wire play prevents an archwire from exerting the desired translational force to move a tooth in the buccal or lingual direction. According to yet another preferred embodiment of the invention, this deficiency can be offset by properly moving the sliding segment of the archwire along y-axis. In order to explain this embodiment of the invention, reference is made again back to FIG. 2A. The archwire sliding segment 120 is moved along y-axis 126 either in the buccal direction if the buccal translation is desired, or in the lingual direction if the lingual translation is desired. O-rings or wire-ties are placed on the bracket in order to keep the archwire within the bracket slot and can be used to achieve the buccal movement. On the other hand when the translational movement of the archwire segment in the lingual direction is required then the archwire is moved in the lingual direction until it comes in firm contact with the bottom of the bracket-slot occupied by the archwire.

As yet another deficiency, the bracket-slot-to-wire play prevents an archwire from exerting the desired translational force to move a tooth in the occlusal or gingival direction. According to yet another preferred embodiment of the invention, this deficiency can be offset by properly moving the sliding segment of the archwire along z-axis. In order to explain this embodiment of the invention, reference is made again back to FIG. 2A. The archwire sliding segment 120 is moved along z-axis 128 either in the occlusal direction if the occlusal translation is desired, or in the gingival direction if the gingival translation is desired. When the translational movement of the archwire segment in the occlusal direction is required then the archwire is moved in the occlusal direction until it comes in firm contact with the lower side wall of the bracket-slot occupied by the archwire. On the other hand when the translational movement of the archwire segment in the gingival direction is required then the archwire is moved in the gingival direction until it comes in firm contact with the upper side wall of the bracket-slot occupied by the archwire.

In summary, the deficiencies caused by the bracket-slot-to-wire play by disabling an archwire from exerting the desired force in any of the 5-degrees of freedom, namely torque (facial and lingual), angulation (mesial and distal), rotation (mesial and distal), buccal and lingual translation and occlusal and gingival translation, can be offset by the various embodiments of the invention disclosed above. A user can manually or automatically identify the type of deficiency caused by the bracket-slot-to-wire play, given bracket slot size and the archwire cross section parameters, and manually or automatically determine the method of offsetting the deficiency, by using the software tools available in the treatment planning workstation. The desired offset for the compensation of the bracket-slot-to-wire play is displayed on the display of the treatment planning workstation. The user can override the offset automatically determined by the treatment planning software and simulate and design the archwire based upon the offset determined to be more desirable by the user or the practitioner. If the desired tooth position cannot be achieved with a single offset, then the practitioner may choose to accomplish that in multiple stages of the tooth movement during the course of the treatment by changing the design of the archwire as the treatment progresses. Also, it is possible that multiple types of deficiencies may be caused by the bracket-slot-to-wire play. In that case the practitioner may choose to combine the remedies for one or more deficiencies using the procedure described above for each degree of freedom, i.e. torque, angulation, rotation and buccal-lingual and occlusal-gingival translations; or approach the remedies in treatment stages.

Figure 9:
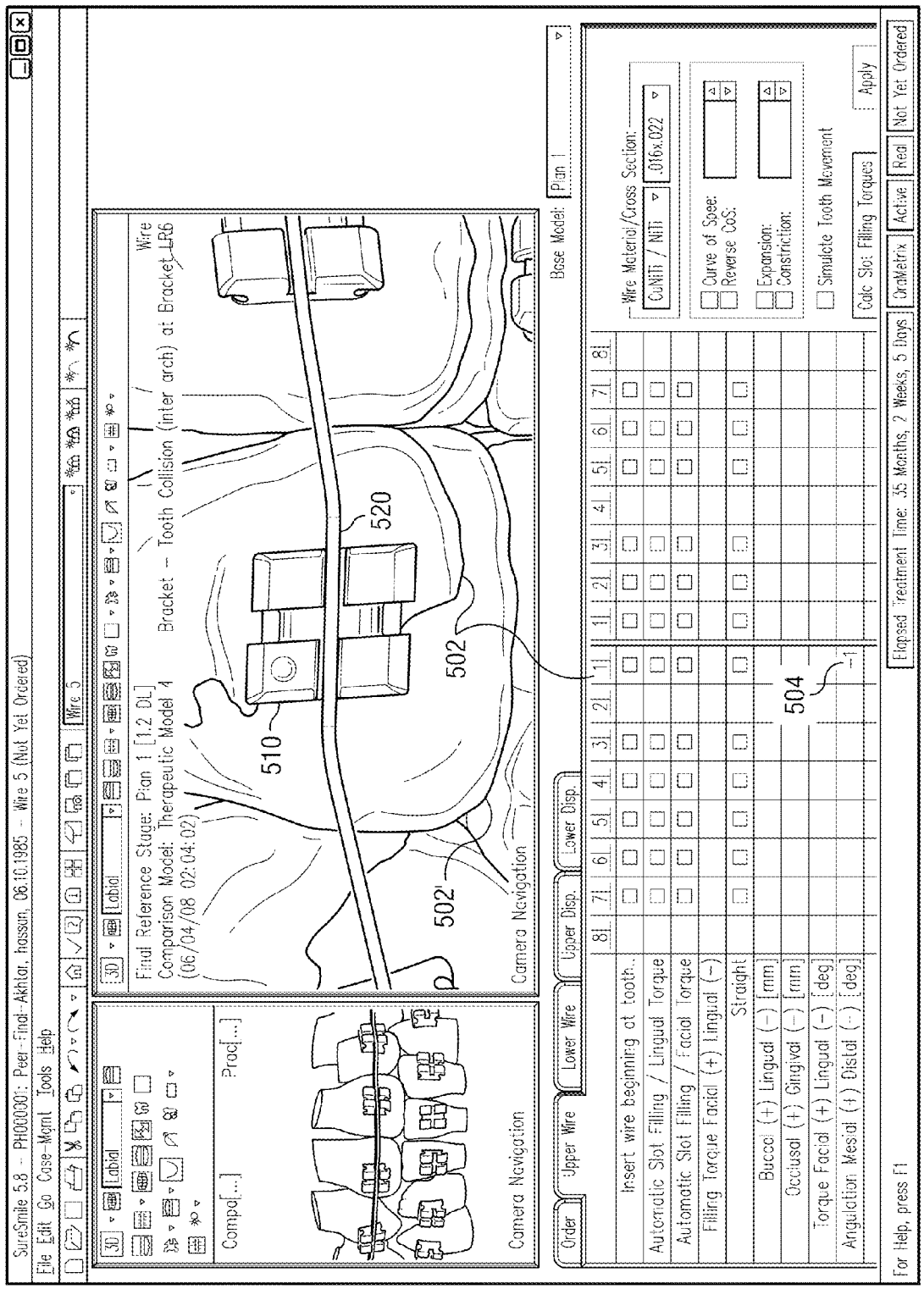
FIG. 9 illustrates the process of designing the desired offset to compensate for the bracket-slot-to-wire play by way of an example.

FIG. 9 illustrates the process of designing the desired offset to compensate for the bracket-slot-to-wire play by way of an example. In this figure, the user has selected tooth 502 in the upper jaw of the patient. Digital or virtual models of the patient's teeth in the initial positions as well as the target or set-up positions are available. FIG. 9 shows a portion of the selected tooth in the initial position 502 along with a portion of the same tooth in the target or set-up position 502'. In this example the desired tooth displacement from the initial position to the target position requires one additional degree of distal angulation 504 (shown as −1 in FIG. 9) to fully engage the bracket slot. The desired displacement can be realized by adjusting the sliding segment 520 of the archwire, which is inserted into the slot of the bracket 510 shown bonded to the tooth in the target position 502', using the procedure described earlier for designing the archwire for handling angulation displacement. The new customized design of the archwire segment to compensate for the bracket-slot-to-wire play will be included in the prescription to bend the archwire. One skilled in the art would appreciate that this methodology of designing the compensation for bracket-slot-to-wire play can be applied to plurality of teeth for designing the customized archwire. The process can be carried out by the practitioner in the practitioner's office, at the 'chair-side while examining the patient' if so desired, or at a different location away from the practitioner's office using the internet as a vehicle of communication between different workstations.

In summary then, according to the preferred embodiment of the invention, the procedure described below is utilized to realize compensation for the bracket-slot-to-wire play.
1. Quantify the bracket-slot-to-wire play.
  (a) This can be accomplished if one of the following items is known.
    i. ideal slot size and ideal archwire cross-section;

ii. tolerance model of slot and tolerance model of the archwire cross-section;

iii. actual (measured) model of slot and actual (measured) model of the archwire cross-section (for each individual item or on a lot bases); or iv. every possible combination of the above three items.

(b) It can be determined from the actual and target positions of bracket slots.

2. Then the offset to compensate for the bracket-slot-to-wire play can be determined as follows:

a. Calculate the slot play between the bracket-slot and the height of the archwire.

b. Calculate the direction of the intended movement in coordinates of the bracket slot. (i.e., initial or actual to target or set-up)

c. Calculate the maximum possible rotation or translation of the archwire sliding segment in the bracket-slot, so that the sides or the edges of the archwire touch the sides of the walls of the bracket-slot, based upon the direction of the information from step 2.b.

The bracket-slot-to-wire play offsetting compensations are made part of the customized archwire design and included in the prescription for manufacturing the customized archwire.

While presently preferred embodiments of the invention have been described for purposes of illustration of the best mode contemplated by the inventors for practicing the invention, wide variation from the details described herein is foreseen without departure from the spirit and scope of the invention. This true spirit and scope is to be determined by reference to the appended claims. The term "bend", as used in the claims, is interpreted to mean either a simple translation movement of the work-piece in one direction or a twist (rotation) of the work-piece, unless the context clearly indicates otherwise.

Compensation Archwire Design Based Upon Progress Model and Target Set-Up

As described earlier, orthodontic arch-wires are used to apply forces to brackets bonded to patients' teeth. The purpose of these arch-wires is to move the teeth into desired positions to achieve some treatment goals. By pre-planning the desired teeth positions using a computer and CAD/CAM software, it is possible to design and produce customized arch-wires which direct tooth movement to pre-planned positions. The arch-wire can be designed by determining desired tooth positions, locating the position and orientation of brackets on each tooth and calculating the shape of an arch-wire that would exert no force when the teeth are in their desired final positions. Once produced and inserted into the brackets on a patient's teeth, the arch-wire acts as a spring forcing the teeth to move toward their intended final positions.

However, a typical orthodontic arch-wire is not able to accomplish all desired movements without auxiliary appliances in all cases. For example, an arch-wire does not exert any force along the length of the wire, so it is not possible to move teeth along the wire without additional appliances. In this case, coil springs or elastics are used to force the teeth to move along the wire. Nor does a typical arch-wire exert forces between teeth in opposing jaws. So, other types of springs or elastics are used to affect inter-arch positioning. Additionally, individual biology can affect the results of an arch-wire. In the majority of cases, auxiliary appliances, such as springs or elastics are applied in conjunction with the archwire. The combination of individual biology and the often used auxiliary appliances results in unknown additional forces applied to the teeth. Thus, a method is required to determine adjusted customized arch-wires and thereby achieve the desired treatment goals and overcome the effects of additional force systems.

Interactive, computer-based treatment monitoring is a significant advantage provided by the treatment planning and appliance design aspects of the system described herein. Typically, when the patient comes into the office during treatment, they will be scanned and a new digital model of the dentition is acquired. From this new model, differences between the current situation and the original malocclusion, and differences between the current situation and the target situation or pre-defined limits or treatment stages as defined earlier can be determined. These differences can be quantified with precision. For example, a point on the tooth in the current model is selected, and the model of the tooth at the original malocclusion is overlaid on the screen. The superposition of the two teeth allows the user to view the change in position that has occurred. The measurement marker features described earlier allow the user to quantify precisely the amount of movement.

Any deviations between the therapeutic result that is observed and the expected result can be captured precisely and at an early stage in treatment using the scanning and treatment planning features described herein, and corrected for. For example, the orthodontist may need to place additional bends in the archwire. Such additional bends can be performed by simulating the wire shape on the screen, displaying the wire only on the screen, and printing out the screen and using it as a template for bending the wire. The current situation could also be forwarded to the precision appliance center for manufacture of a new appliance. Of course, these monitoring and treatment corrections are applicable to any type of appliance selected for the patient.

The adjusted customized arch-wire can be designed after an initial customized arch-wire has been used to treat a patient and is at or near equilibrium. The initial custom arch-wire is first designed by producing a 3D computer-based, geometrical model of a patient's dentition, locating brackets on the digital tooth model, moving the digital tooth models to planned final positions and orientations, and then calculating a wire which fits in the slots of the brackets while the teeth are at their planned final positions and exerts no forces on the brackets. This wire is produced according to the design and delivered to the practitioner who subsequently inserts the wire into the brackets in the patient's mouth. After a period of time the teeth will move under the force of the wire and will eventually move into positions such that the forces from all appliances and biological systems are in equilibrium. If the teeth are not in the final planned positions at that point in time, the adjusted custom arch-wire is designed and applied.

The design of the adjusted wire is accomplished first by making a 3D computer-based geometrical model of the positions of teeth at equilibrium. This model is referred to as a progress model because it captures the treatment progress. This model can be produced via scanning the tooth positions and processing the scan data into models or by moving the tooth models interactively in a computer-based software system to estimate the actual tooth positions in the mouth.

Then, tooth by tooth differences in all 6 degrees of freedom (three positional directions and three rotational directions) between the desired final tooth positions and the progress model tooth positions are calculated. These differences are then added to the initial custom wire design to determine the adjusted custom wire design. For example, if the original plan called for the movement of a tooth by 1 mm in the anterior direction, but after treatment with the initial custom wire, only 0.75 mm of movement was realized. Then, a new adjusted custom arch-wire can be made by adding an additional 0.25 mm offset in the anterior direction to compensate for other forces acting on the tooth.

Figure 10:
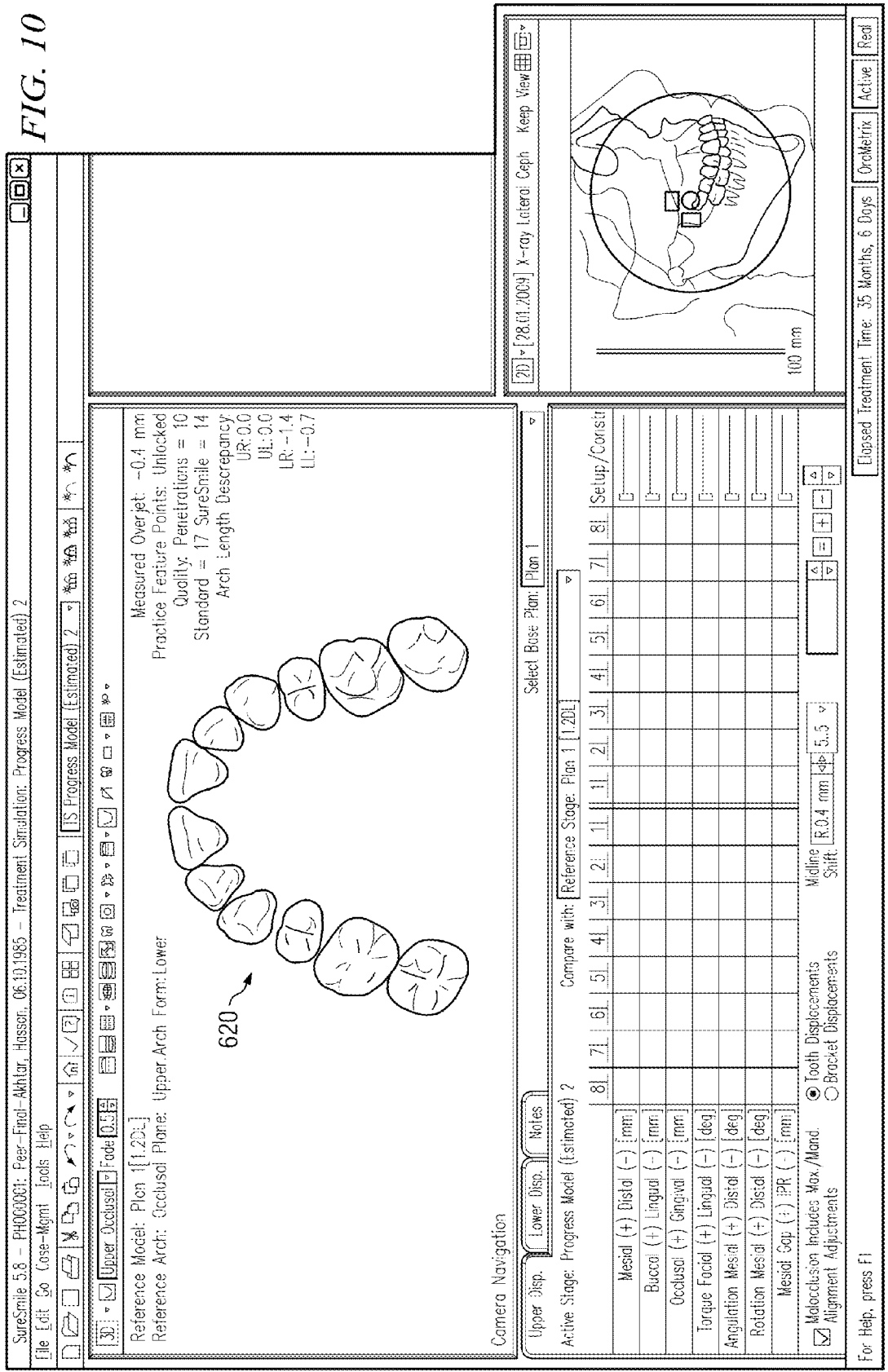
FIG. 10 shows an example digital or virtual target setup model of a patient's dentition.

FIG. 10 shows a screen shot of an example digital or virtual target setup model of the dentition 620 of a patient. The model shown is for the upper jaw. This model was developed during the treatment planning phase for the patient. This model shows the desired final position of teeth to be realized at the end of the treatment.

Figure 11:
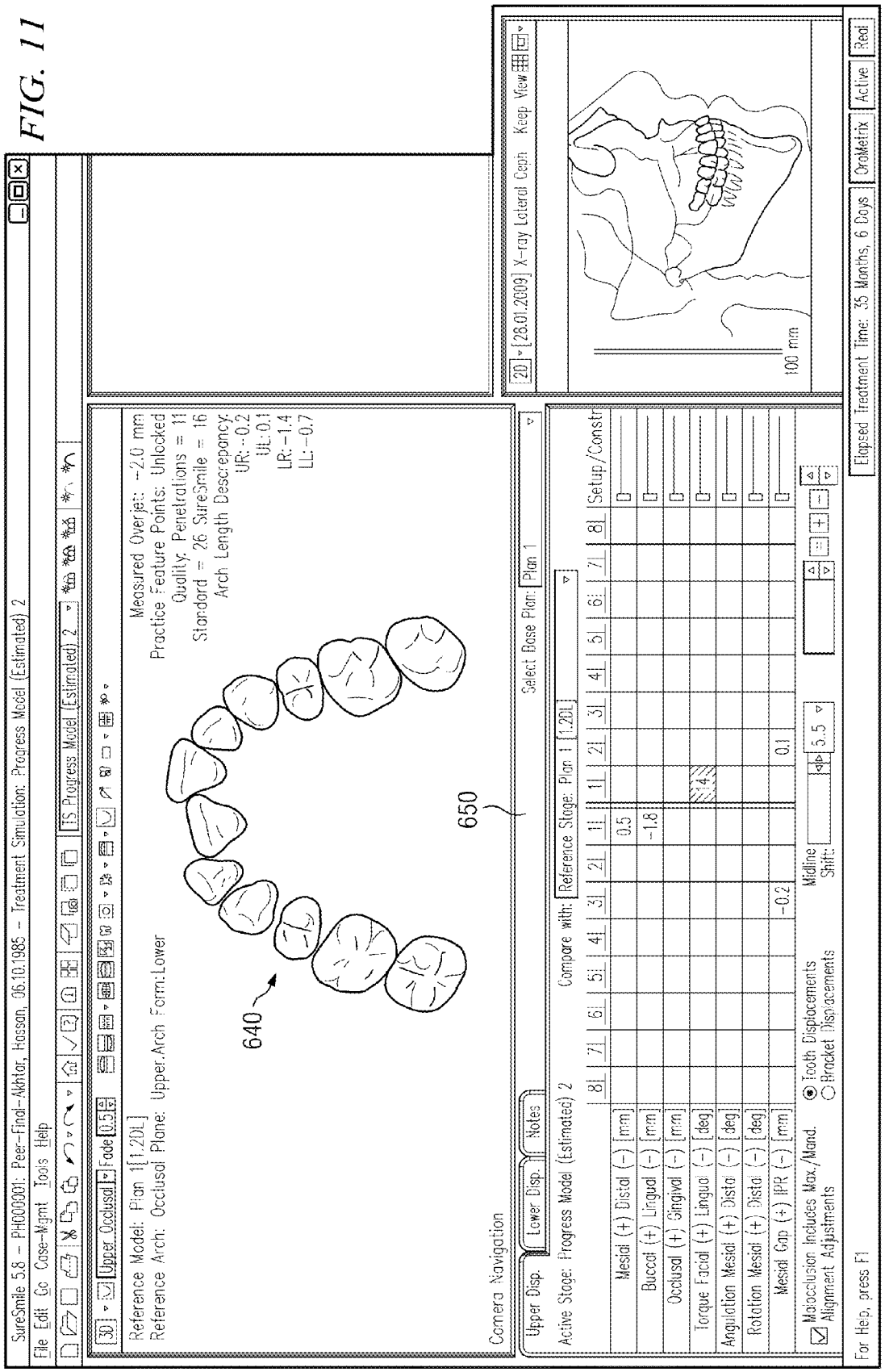
FIG. 11 shows the three-dimensional digital or virtual progress model of the current state of the dentition of the same patient as in FIG. 10. The figure also lists the nature and amount of displacement still required for each tooth relative to the target setup.

FIG. 11 shows the three-dimensional digital or virtual progress model 640 of the current state of the dentition of the same patient as in FIG. 10. Here also, the model shown is for the upper jaw. Nature and amount of displacement still required for each tooth relative to the target setup is listed in table 650. The displacements are automatically calculated by the treatment planning software and displayed on the display of the treatment planning workstation. According to a preferred embodiment of the invention, this model is arrived at by the treatment planner by manipulating the target setup model of FIG. 10 to match either the visually observed state of the teeth during the treatment monitoring visit by the patient, or the recent photographs of the dentition of the patient. Alternately, this model is obtained by scanning the dentition of the patient during treatment monitoring. In a preferred embodiment of the invention described herein the scanning is done in-vivo. Alternately, an impression of the patient's dentition may be taken; and the scanning of the impression or the physical model developed from the impression can be done.

Figure 12:
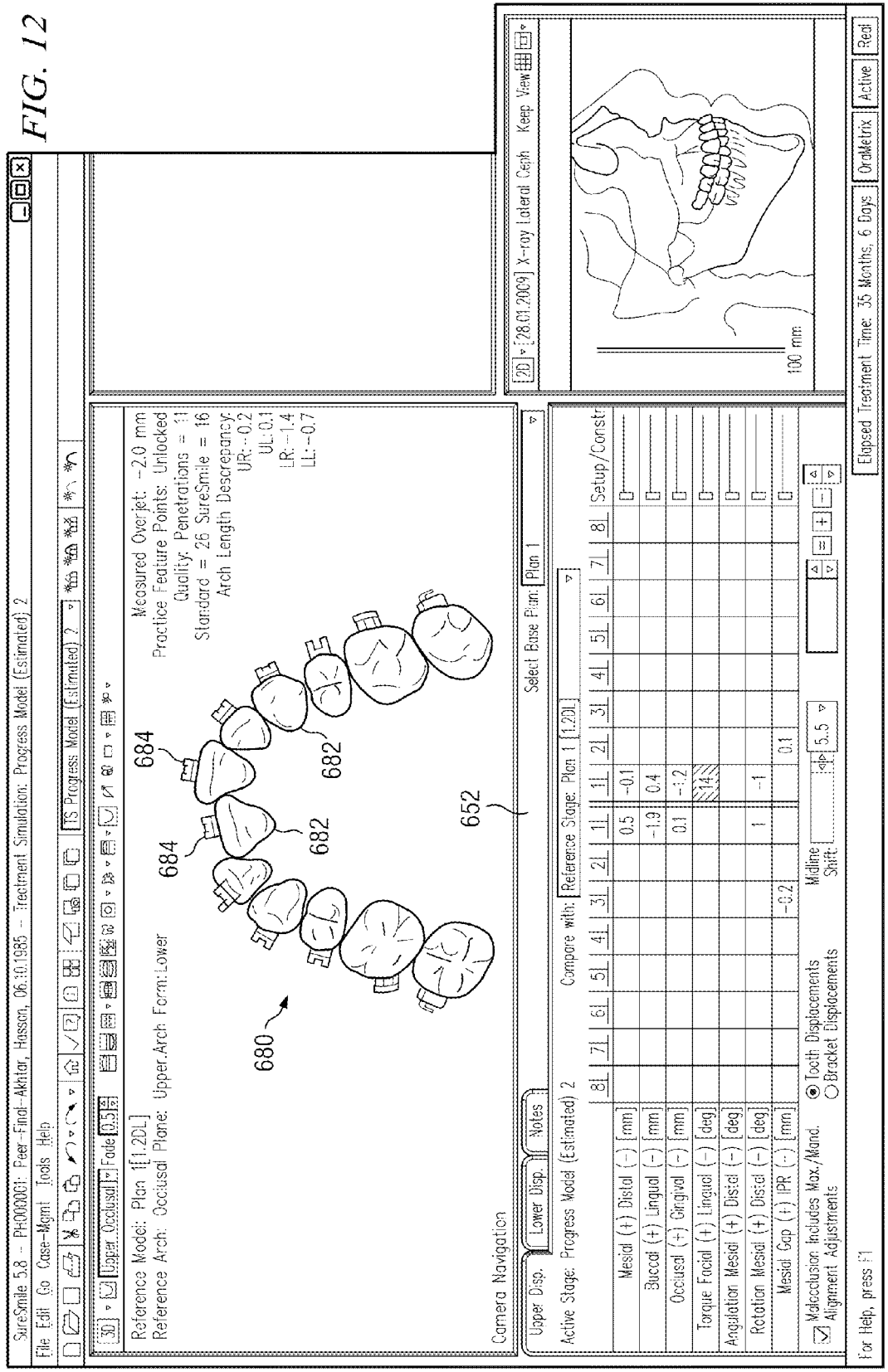
FIG. 12 shows the virtual progress model with the brackets attached to the teeth.

FIG. 12 shows the virtual model 680 wherein the brackets 684 are attached to the teeth 682. The teeth positions shown in FIG. 12 represent the progress model shown in FIG. 11. Furthermore, nature and amount of displacement still required for each bracket bonded to a tooth relative to the target setup is listed in table 652. These displacements are also automatically calculated by the treatment planning software.

Figure 13:
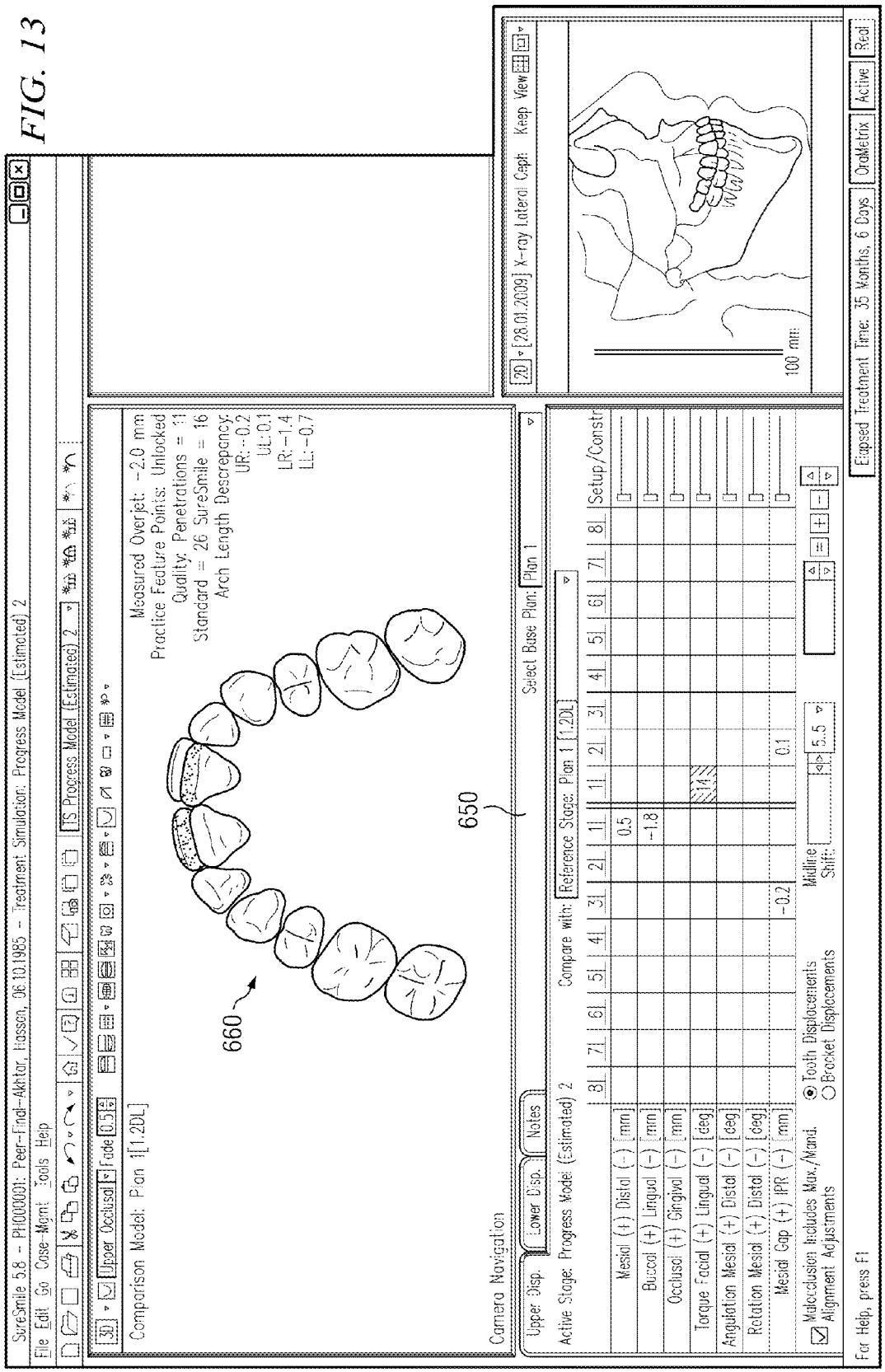
FIG. 13 shows a superimposed virtual model of the patient's dentition obtained by combining the target set-up model of FIG. 10 with the progress model of FIG. 11.
Figure 13A:
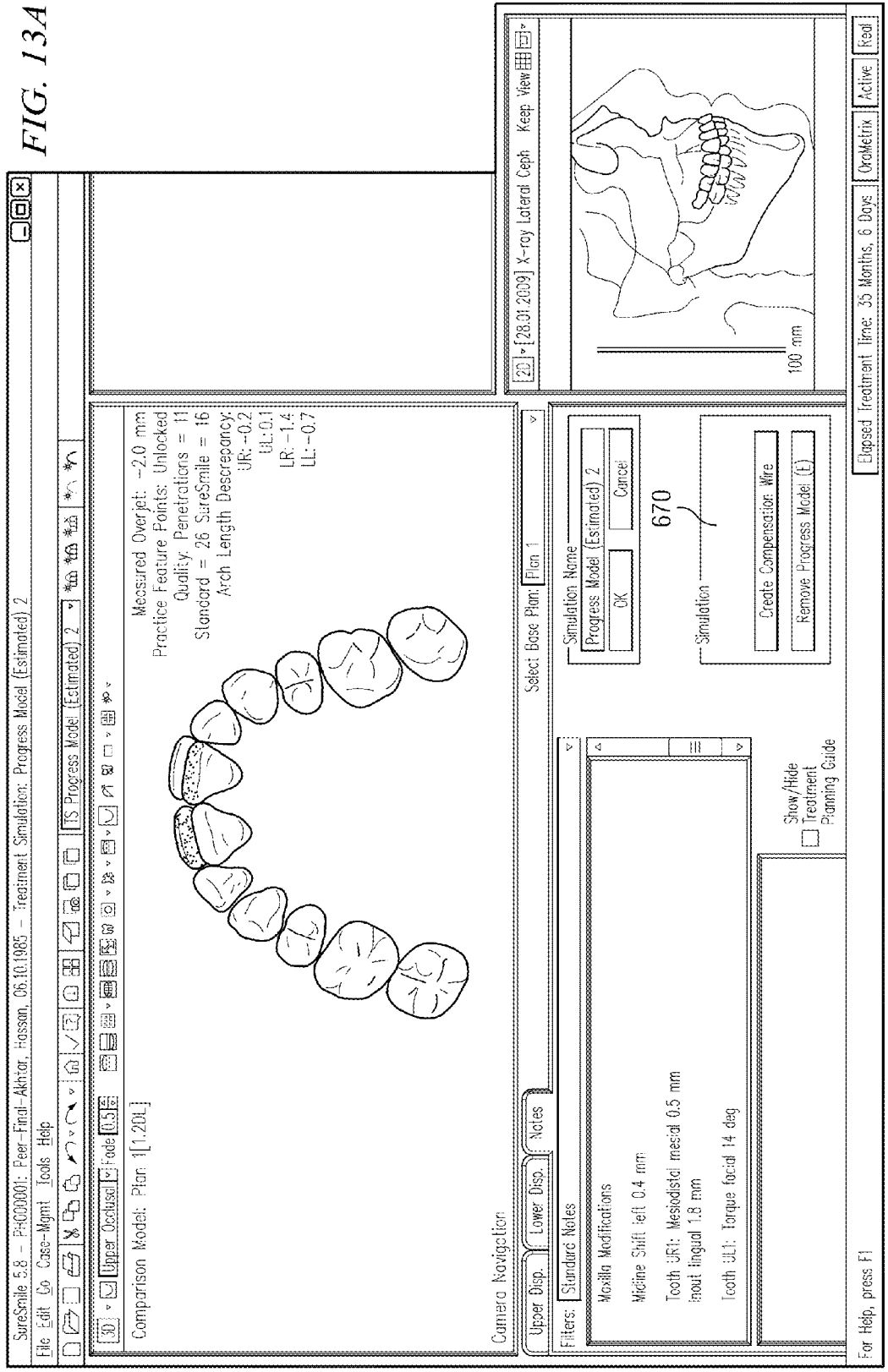
FIG. 13A shows 'Create Compensation Wire' tab on the treatment planning workstation display.

FIG. 13 shows a superimposed virtual model 660 of the patient's dentition obtained by combining the target set-up model 620 of FIG. 10 with the progress model 640 of FIG. 11. Virtual model 660 provides visualization of the displacements still remaining between the actual positions of the teeth and the desired positions of the teeth. Table 650 shows the same tooth displacement data as in FIG. 11. The treatment planner can now automatically design the compensation archwire by selecting 'Create Compensation Wire' tab 670 on the treatment planning workstation display shown in FIG. 13A.

Figure 14:
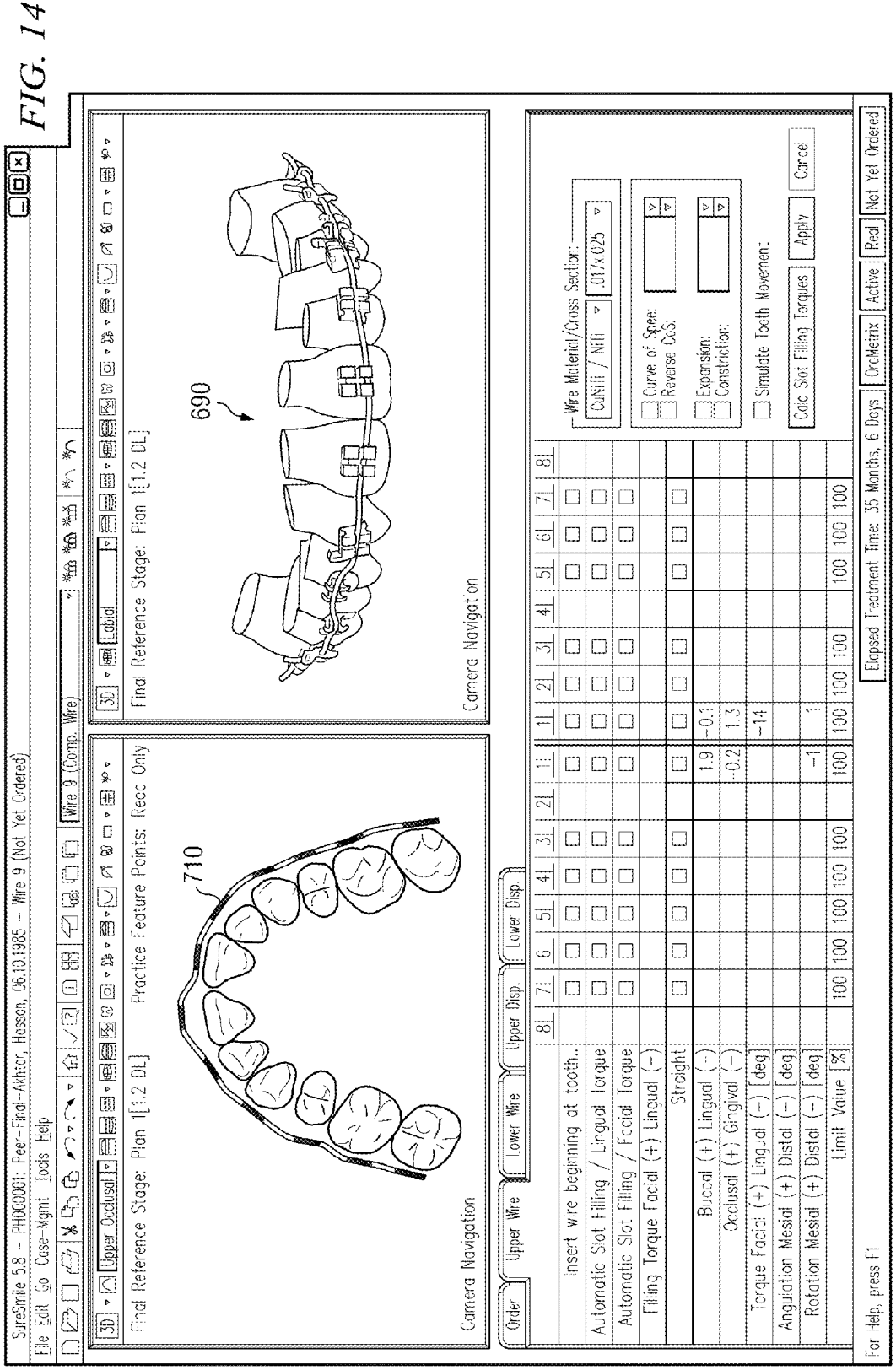
FIG. 14 shows the virtual target set-up model of the patient's dentition previously shown in FIG. 10; and the shape of the newly designed archwire in order to compensate for deviations between the target setup and the progress model. Also shown in FIG. 14 is the virtual model showing teeth, brackets and the compensation archwire.

FIG. 14 shows the virtual target set-up model of the patient's dentition previously shown in FIG. 10; and the shape of the newly designed archwire 710 in order to compensate for deviations between the target setup and the progress model. Also shown in FIG. 14 is the virtual model 690 showing teeth, brackets and the compensation archwire.

Figure 15:
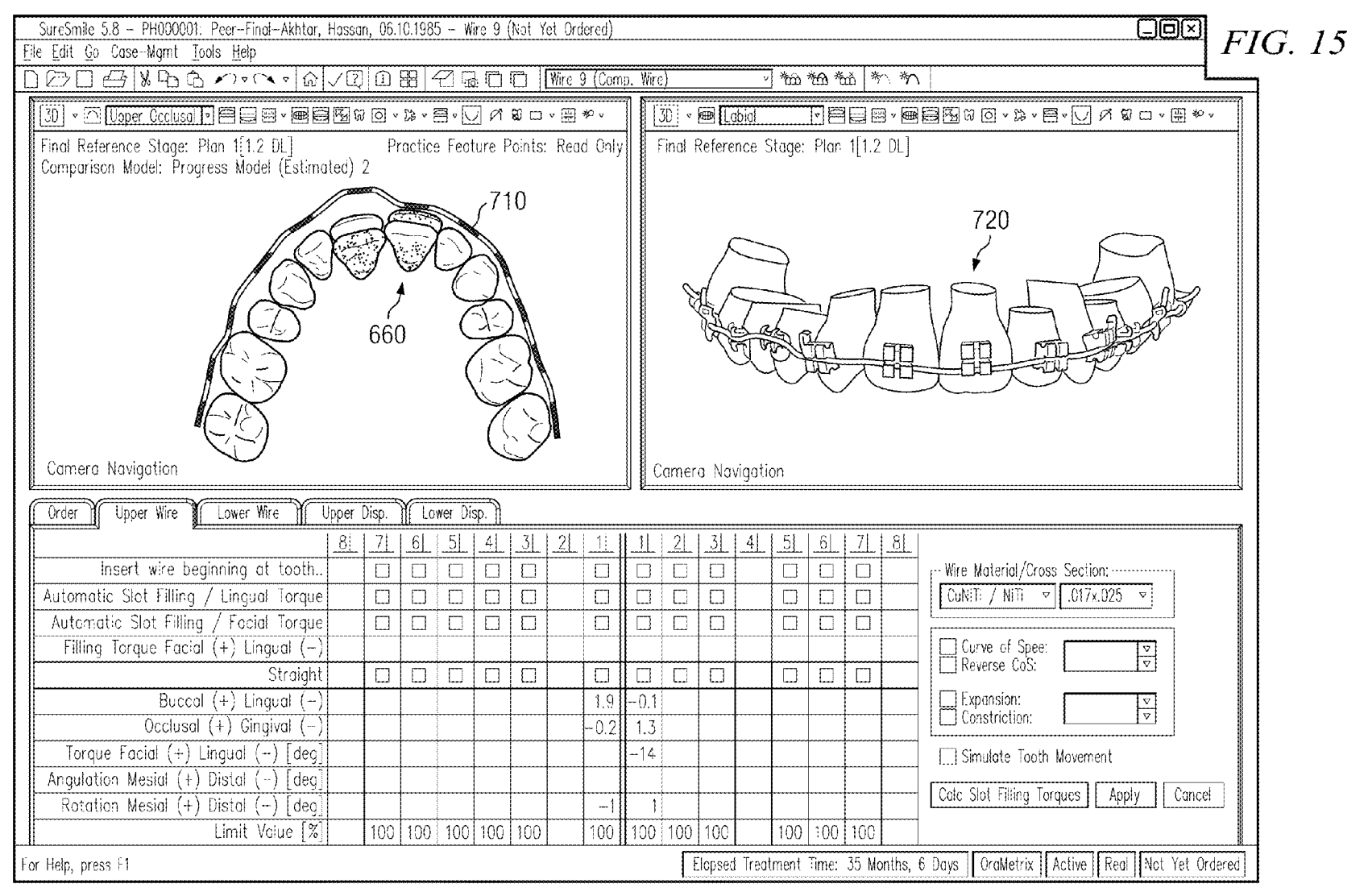

FIG. 15 shows the virtual superimposed model 660 the same as in FIG. 13 along with the newly designed compensation archwire 710. Also shown is a model 720 of the teeth, brackets and archwire.

Figure 16A:
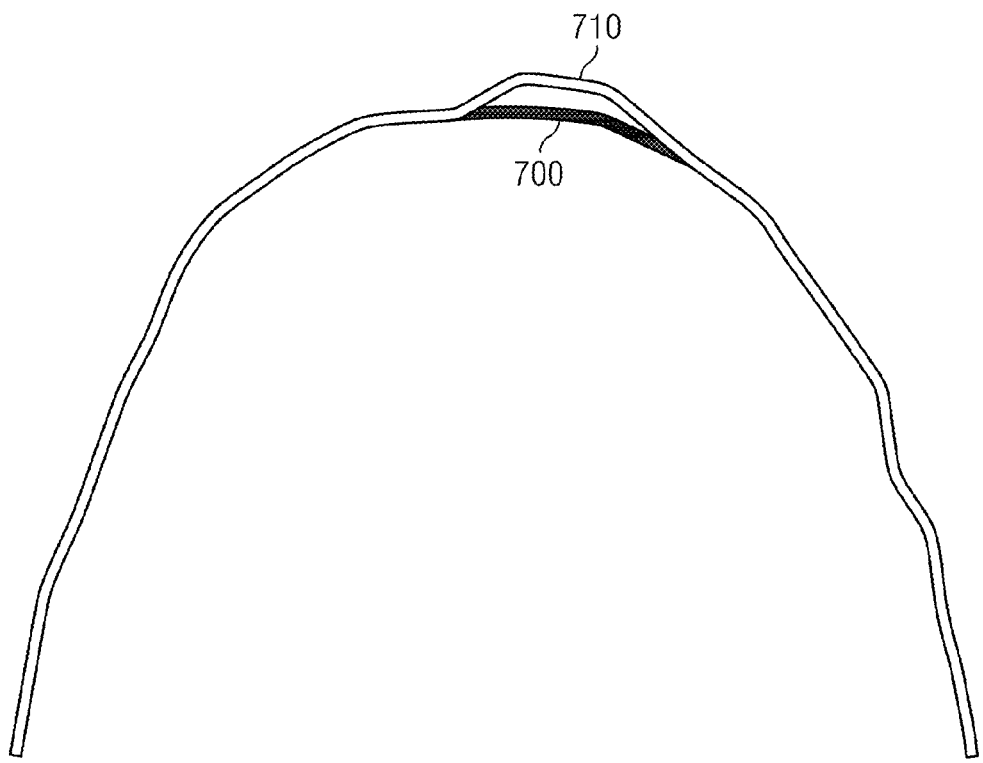
FIG. 16A shows the comparison between the set-up archwire and the newly designed compensation archwire both shown in the arch form.

FIG. 16A shows the comparison between the set-up archwire 700 and the newly designed compensation archwire 710 both shown in the arch form.

Figure 16B:
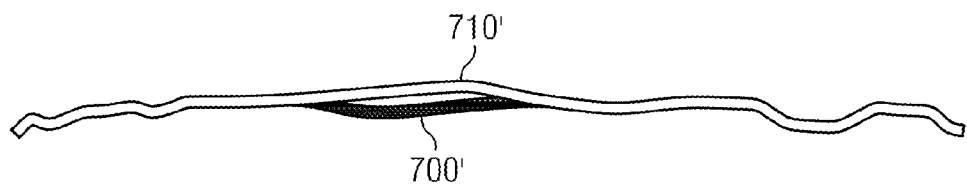
FIG. 16B shows the same two wires as in FIG. 16A, but from the archwire plane view perspective.

FIG. 16B shows the same two wires as in FIG. 16A, but from the archwire plane view perspective 700' and 710'.

In summary, often the initially designed customized arch-wire for moving a patient's teeth from malocclusion to the desired target set-up reaches an equilibrium without achieving the planned treatment goal. In such a case the current or progress model of the patient's teeth shows tooth displacements required to achieve the target positions. The preferred embodiment of the invention disclosed herein enables the practitioner evaluate the progress model in order to determine the tooth displacements still required to move the teeth in the desired positions; and design the compensation archwire by making adjustments necessary to the initial design of the arch wire. The compensations can be made to achieve displacements in all 6 degrees of freedom, i.e. misial or distal translational displacement, buccal or lingual translational displacement; occlusal or gingival translational displacement, facial or lingual torque, mesial or distal angulation and mesial or distal rotation. The treatment planning software performs calculations automatically to determine the extent and the nature of displacements required from the three dimensional digital models of progress and the target. The practitioner can look at the displacements and if they are satisfactory, then instructs the workstation to perform the compensation design of the archwire automatically. The workstation provides the tools whereby the practitioner can override one or more displacements that were automatically calculated by the treatment planning workstation; and specify new values for the selected displacements. Then the compensation archwire design is performed using the displacement parameters specified by the practitioner or the treatment planner. The complete compensation archwire design can be carried out by the practitioner at patient's 'chair side' at the practitioner's practice or by a treatment planner at a remote location and can be communicated to the practitioner via internet communications. The compensation design can be simulated by varying the displacement parameters using the treatment planning workstation so as to evaluate multiple options for the compensation design of the archwire.

The process can be summarized as follows:

A method of designing the shape of a compensating orthodontic arch-wire inserted into slots of brackets bonded to teeth of an orthodontic patient is disclosed based upon progress model of treatment and initial archwire design, utilizing a workstation. The steps comprise:

a. retrieving a three-dimensional digital model of the target positions of the teeth of an orthodontic patient;

b. retrieving initial design of the archwire customized to move the patient's teeth from malocclusion to target set-up;

c. obtaining a three-dimensional digital model of the current positions of the teeth of the orthodontic patient;

d. computing differences in 3 translational degrees of freedom and 3 rotational degrees of freedom between the target positions of teeth and the current positions of teeth per the progress model; and e. designing shape of the compensating orthodontic arch-wire based upon adding said differences to the initial design of the archwire performed to move the teeth in the initial position or malocclusion to the target or desired final position or set-up.

The design of the initial archwire is performed as follows:

i. obtaining a digital model of the malocclusion of the patient's teeth;

ii. performing treatment planning simulation using the digital model of the malocclusion; thereby obtaining a three-dimensional digital model of target positions of the teeth from the digital model of the malocclusion. The digital model of malocclusion of the patient's teeth can be obtained by in-vivo scanning said patient's dentition, or by scanning an impression of the patient's dentition, or by scanning a physical model of the patient's dentition. The current positions of teeth of an orthodontic patient can be arrived at by a practitioner by manipulating the three-dimensional digital model of the target positions of teeth of the orthodontic patient to match with visually observed state of teeth of the patient during a treatment monitoring visit by the patient. Alternately, the current positions of teeth of the orthodontic patient can be arrived at by a practitioner by manipulating the three-dimensional digital model of the target positions of teeth of the orthodontic patient to match with recent photographs, which may be taken at the practitioner's office, or are otherwise available, of the dentition of the patient. Alternately, the current position of teeth of the orthodontic patient is arrived at by the practitioner by in-vivo scanning the teeth of the patient during a treatment monitoring session; or by scanning an impression or a physical model made from the impression of the patient's dentition. Additionally, the tooth displacements that can be attributed to the bracket-slot-to-wire play in the progress model can also be addressed as a part of the compensation archwire design. As described earlier, displacements in 5 degrees of freedom can be handled through offsetting the bracket-slot-to-wire play by additional compensations of the archwire design.

While presently preferred embodiments of the invention have been described for purposes of illustration of the best mode contemplated by the inventors for practicing the invention, wide variation from the details described herein is foreseen without departure from the spirit and scope of the invention. This true spirit and scope is to be determined by reference to the appended claims. The term "bend", as used in the claims, is interpreted to mean either a simple translation movement of the work-piece in one direction or a twist (rotation) of the work-piece, unless the context clearly indicates otherwise.

The invention claimed is:

1. A method of designing shape of a compensating orthodontic arch-wire during orthodontic treatment of a patient based upon progress observed during monitoring of the treatment, utilizing a workstation, comprising the steps of:
   a. retrieving a three-dimensional digital model of target positions of teeth of said orthodontic patient in said workstation;
   b. retrieving a three-dimensional digital model of initial design of archwire with customized shape to move said patient's teeth from malocclusion to said target positions in said workstation;
   wherein a real archwire is designed in accordance with said initial design and inserted into slots of brackets bonded to said patient's teeth to begin said orthodontic treatment;
   c. obtaining a three-dimensional digital progress model of current positions of said teeth of said orthodontic patient during said orthodontic treatment and storing it in said workstation;
   wherein said three-dimensional digital progress model is obtained when said real archwire loses said customized shape and is at or near equilibrium;
   d. computing differences in 3 translational degrees of freedom and 3 rotational degrees of freedom between said target positions of teeth and said current positions of teeth in said progress model using instructions in said workstation; and
   e. designing shape of said compensating orthodontic arch-wire based upon adding said differences to said initial design of said archwire using instructions in said workstation.

2. The method of claim 1, wherein said three-dimensional digital model of target positions of teeth is obtained through the steps comprising:
   i. scanning malocclusion of said patient's teeth;
   ii. deriving a digital model of said malocclusion using data obtained from said scanning step; and
   iii. performing treatment planning simulation using said digital model of said malocclusion; thereby obtaining said three-dimensional digital model of target positions of teeth from said digital model of said malocclusion.

3. The method of claim 2, wherein in step i scanning is performed by in-vivo scanning said patient's dentition.

4. The method of claim 2, wherein in step i scanning is performed by scanning an impression of said patient's dentition.

5. The method of claim 2, wherein in step i scanning is performed by scanning a physical model of said patient's dentition.

6. The method of claim 1, wherein said current positions of said teeth of said orthodontic patient is arrived at by a practitioner by manipulating said three-dimensional digital model of target positions of teeth of said orthodontic patient to match with visually observed state of said teeth of said patient during a treatment monitoring visit by said patient.

7. The method of claim 1, wherein said current positions of said teeth of said orthodontic patient is arrived at by a practitioner by manipulating said three-dimensional digital model of target positions of teeth of said orthodontic patient to match with recent photographs of said dentition of said patient.

8. The method of claim 1, wherein said current positions of said teeth of said orthodontic patient is arrived at by a practitioner by in-vivo scanning said teeth of said patient during treatment monitoring.

9. The method of claim 1, wherein said current positions of said teeth of said orthodontic patient is arrived at by scanning an impression of said patient's dentition.

10. The method of claim 1, wherein said current positions of said teeth of said orthodontic patient is arrived at by scanning a physical model said patient's dentition.

11. The method of claim 1, wherein said differences in 3 translational degrees of freedom comprise misial or distal translational displacement; buccal or lingual translational displacement; and occlusal or gingival translational displacement.

12. The method of claim 1, wherein said differences in 3 rotational degrees of freedom comprise facial or lingual torque, mesial or distal angulation and mesial or distal rotation.

13. The method of claim 1, wherein said compensating orthodontic arch-wire design can be carried out by a practitioner at said patient's 'chair side' at said practitioner's practice.

14. The method of claim 1, wherein said compensating orthodontic arch-wire design includes rotation of straight wire segment for slot filling torque.

15. The method of claim 1, wherein an orthodontist may need to place additional bends in said compensating orthodontic archwire; wherein said additional bends can be performed by simulating said compensating orthodontic arch-wire shape on said workstation screen, displaying only said compensating orthodontic archwire on said screen, printing out said screen and using it as a template for bending said compensating orthodontic archwire.

* * * * *